(12) United States Patent
Larmer et al.

(10) Patent No.: US 10,709,631 B2
(45) Date of Patent: Jul. 14, 2020

(54) COMPRESSION GARMENT FOR NEUROLOGICAL AND CIRCULATORY DISORDERS

(71) Applicant: MEDI USA, L.P., Whitsett, NC (US)

(72) Inventors: Kevin Larmer, San Diego, CA (US); Moses Lipshaw, Encinitas, CA (US); Thomas Richardson, San Diego, CA (US); Karen Lynch, San Diego, CA (US); Glenn Anderson, Whitsett, NC (US); Dean Bender, Terrell, NC (US); Chris Majors, Whitsett, NC (US); Mary Sorg, Waterford, PA (US)

(73) Assignee: MEDI USA, L.P., Whitsett, NC (US)

( * ) Notice: Subject to any disclaimer, the term of this patent is extended or adjusted under 35 U.S.C. 154(b) by 436 days.

(21) Appl. No.: 15/467,902

(22) Filed: Mar. 23, 2017

(65) Prior Publication Data
US 2017/0273851 A1 Sep. 28, 2017

Related U.S. Application Data

(60) Provisional application No. 62/313,632, filed on Mar. 25, 2016.

(51) Int. Cl.
*A61H 1/00* (2006.01)
*A61F 13/06* (2006.01)
(Continued)

(52) U.S. Cl.
CPC ........... *A61H 1/008* (2013.01); *A61F 13/067* (2013.01); *A61F 13/08* (2013.01); *A61H 9/0092* (2013.01);
(Continued)

(58) Field of Classification Search
CPC ...... A61H 1/008; A61H 39/04; A61H 9/0092; A61H 2205/12; A61H 2205/125;
(Continued)

(56) References Cited

U.S. PATENT DOCUMENTS 1,443,844 A * 1/1923 Jensen .................. A61F 13/066
602/66
1,538,026 A * 5/1925 Cramer ................. A61F 13/065
602/66
(Continued)

*Primary Examiner* — Bradley H Philips
*Assistant Examiner* — Vincent D Hoang
(74) *Attorney, Agent, or Firm* — Rimon, P.C.

(57) ABSTRACT

A compression garment for a neurological disorder includes a body portion and a pad. The body portion may be operable to wrap around a foot and the pad can attach to an inner surface of the body portion. The pad can include an outward protrusion and/or an inward recess. A guide sleeve may be dimensioned to wrap together with the body portion around the foot, the pad being disposable between the body portion and the guide sleeve. A first tensioning band may be attached onto to first and second locations of the body portion and be operable to secure opposing first and second portions of the inner surface of the body portion to secure the outward protrusion and/or recess of the pad against the abductor hallucis and flexor hallucis brevis muscles of the foot. The outward protrusion can include a receiver for the metatarsal head.

16 Claims, 13 Drawing Sheets

(51) Int. Cl.
*A61H 9/00* (2006.01)
*A61H 39/04* (2006.01)
*A61F 13/08* (2006.01)
*A43B 7/14* (2006.01)
*A43B 3/00* (2006.01)
*A43B 17/00* (2006.01)

(52) U.S. Cl.
CPC ............ *A61H 39/04* (2013.01); *A43B 3/0005* (2013.01); *A43B 7/146* (2013.01); *A43B 7/147* (2013.01); *A43B 7/1415* (2013.01); *A43B 7/1425* (2013.01); *A43B 7/1435* (2013.01); *A43B 17/00* (2013.01); *A61H 2201/0103* (2013.01); *A61H 2201/0192* (2013.01); *A61H 2201/0207* (2013.01); *A61H 2201/0214* (2013.01); *A61H 2201/5012* (2013.01); *A61H 2201/5048* (2013.01); *A61H 2201/5058* (2013.01); *A61H 2201/5061* (2013.01); *A61H 2201/5084* (2013.01); *A61H 2201/5097* (2013.01); *A61H 2205/12* (2013.01); *A61H 2205/125* (2013.01)

(58) Field of Classification Search
CPC .... A61H 2201/0214; A61H 2201/0192; A61H 2201/0207; A61H 2201/5061; A61H 2201/5058; A61H 2201/5084; A61H 2201/5097; A61H 2201/5048; A61H 2201/5012; A61H 2201/0103; A61H 2201/5071; A43B 7/146; A43B 7/147; A43B 7/149; A61F 13/08; A61F 13/067; A61F 13/064
USPC ...................... 36/43; 601/148, 151, 150, 134
See application file for complete search history.

(56) References Cited

U.S. PATENT DOCUMENTS

| | | | | |
|---|---|---|---|---|
| 1,651,285 | A | * | 11/1927 | Levick, Jr. ............ A61F 13/065 602/66 |
| 3,093,130 | A | * | 6/1963 | Cotton ................. A61F 13/064 602/29 |
| 4,227,320 | A | * | 10/1980 | Borgeas ................ A43B 17/03 36/29 |
| 4,614,179 | A | * | 9/1986 | Gardner ............... A61H 9/0078 128/DIG. 20 |
| 5,263,473 | A | | 11/1993 | McWhorter |
| 5,989,204 | A | | 11/1999 | Lina |
| 6,685,661 | B2 | | 2/2004 | Peled |
| 7,753,867 | B2 | * | 7/2010 | Sorg ..................... A43B 7/1425 128/112.1 |
| 2005/0143682 | A1 | | 6/2005 | Cook et al. |
| 2005/0192524 | A1 | * | 9/2005 | Lipshaw ................ A61F 13/06 602/62 |
| 2009/0024066 | A1 | | 1/2009 | Sorg |
| 2013/0319128 | A1 | * | 12/2013 | Richardson ............ G01N 3/08 73/818 |

* cited by examiner

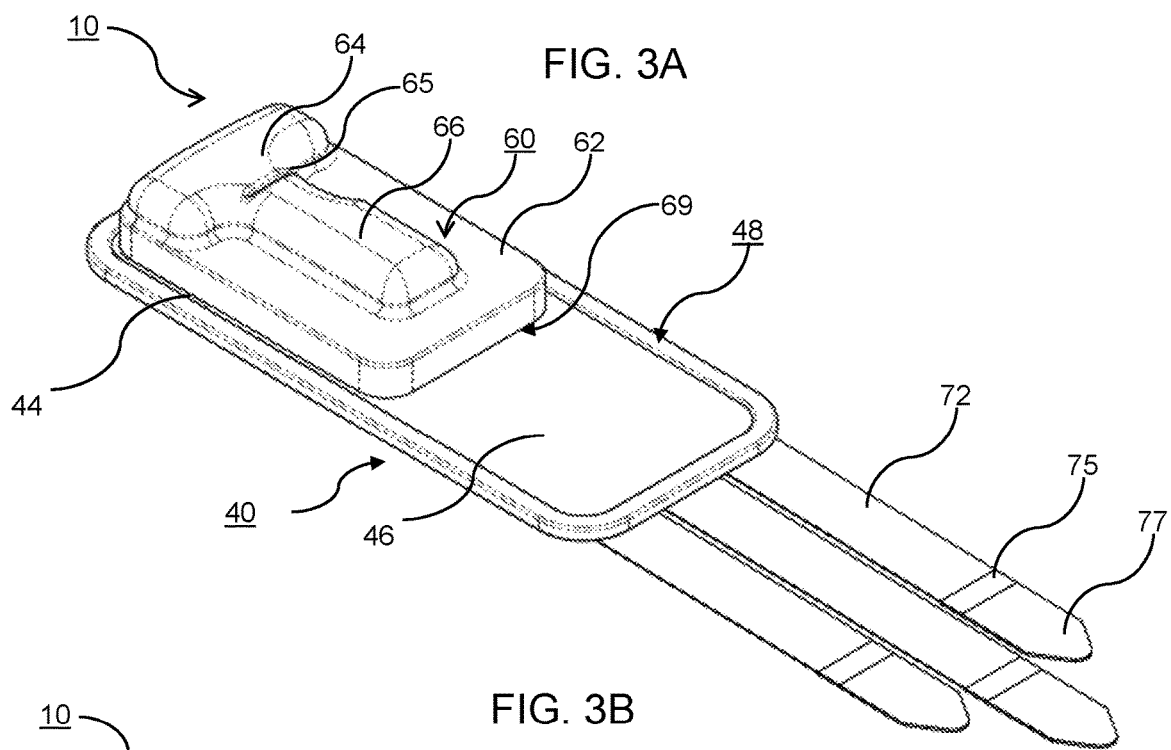
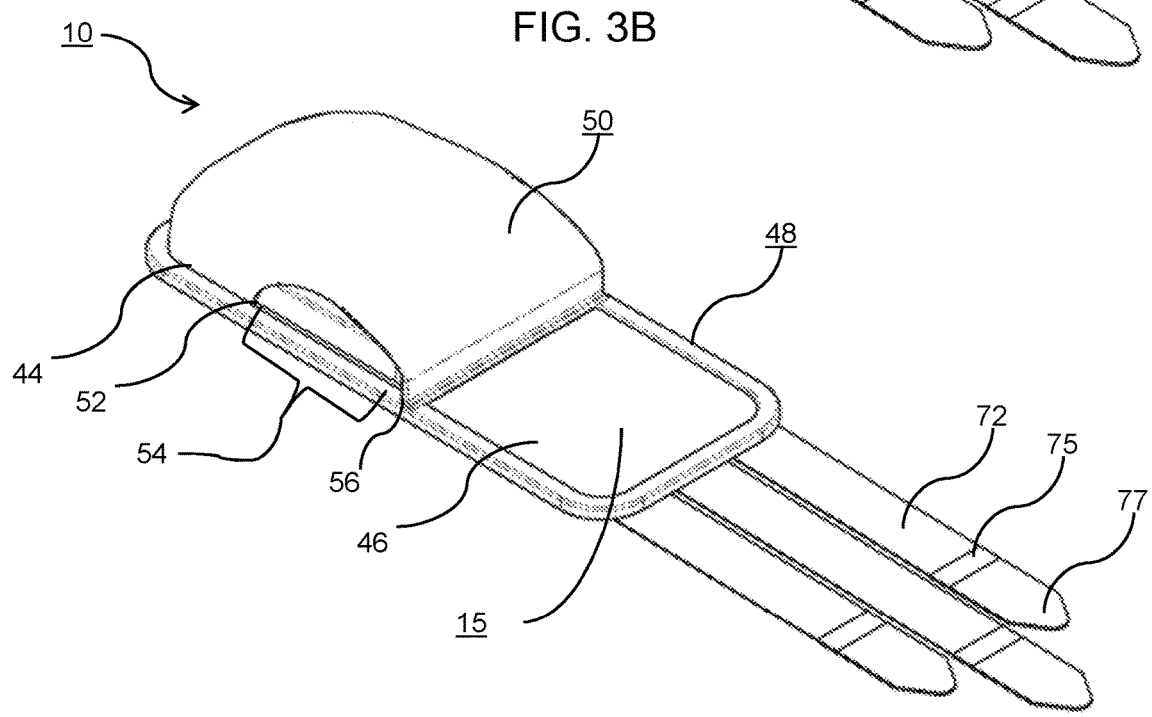

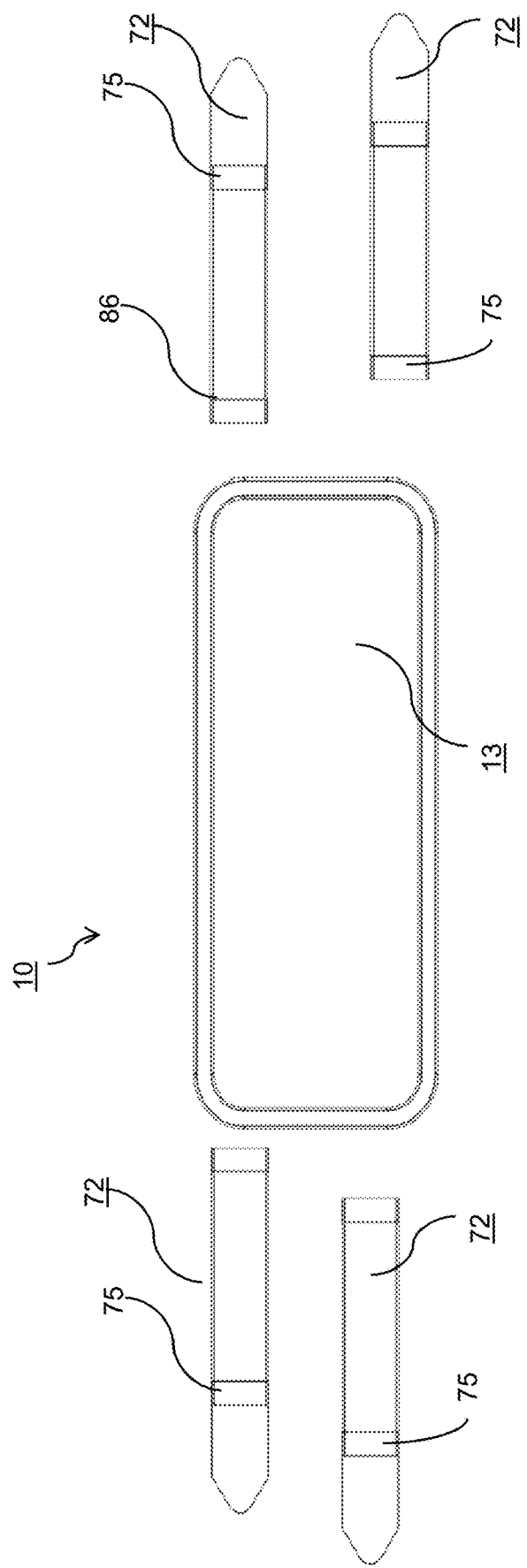

COMPRESSION GARMENT FOR NEUROLOGICAL AND CIRCULATORY DISORDERS

CROSS REFERENCE TO RELATED APPLICATIONS

This application claims priority from U.S. Provisional Application Ser. No. 62/313,632 filed Mar. 25, 2016, which is incorporated herein by reference in its entirety as set forth below.

FIELD

The present disclosure relates generally to garments for treatment of neurological conditions and circulatory disorders.

BACKGROUND

The foot is one of the most complicated and sophisticated of all body parts or appendages. However, its care and maintenance is generally neglected until an affliction or injury occurs. One affliction that can occur with the foot is metatarsalgia which is a type of foot pain that occurs in the ball of the foot that can impede walking and standing. Another affliction that can occur with a foot is excess pronation. Excess pronation is a problem that occurs as part of the process of human gait and if untreated, this can lead to progressive bone deformities. Another affliction common to the foot is plantar fasciitis, wherein heel spurs and other types of plantar facial pain are felt by a subject. Current approaches to plantar fasciitis include relaxing the musculature of the foot and this can be accomplished using braces and splints. Other common afflictions of the foot can include issues related to the arch. Arch support orthotics have therefore been designed to be disposed upon the inner sole of the shoe for building up the shoe and supporting the arch of the foot.

One particular affliction of amorphous etiology is restless leg syndrome (RLS). RLS can manifest itself in various ways such as by ineluctable creeping sensations and internal itching sensations occurring in the lower extremities. Symptoms can also be more pronounced at the end of the day when an individual is seated or in a supine position. When symptoms are particularly aggravated, one typical approach for relief is for the individual to move his or her legs. However, because RLS can occur for long periods of time including throughout the night, individuals can become frustrated and be incapable of attaining a sound and restful sleep.

It is with respect to these and other considerations that the various embodiments described below are presented.

SUMMARY

In certain embodiments, a compression garment is provided for a neurological disorder, such as Restless Leg Syndrome. The garment can include a body portion and a pad. The body portion may be operable to wrap around a foot and the pad can attach to an inner surface of the body portion in a predetermined position. The pad can include an outward protrusion and/or an inward recess. A guide sleeve may be dimensioned to wrap together with the body portion around the foot, the pad being disposable between the body portion and the guide sleeve. A first tensioning band may be attached onto to first and second locations of the body portion and be operable to secure opposing first and second portions of the inner surface of the body portion to secure the outward protrusion and/or recess of the pad against the abductor hallucis and flexor hallucis brevis muscles of the foot. The outward protrusion can include a receiver for the metatarsal head.

The outward protrusion of the pad may include a receiver formed for a metatarsal head of the foot. The receiver may be formed at a vertex of perpendicularly arranged members of the outward protrusion. In this respect, the outward protrusion may be a T-shaped member. The outward protrusion may also be oriented to apply contact across a predetermined region of the foot when the garment is in a wrapped position with the foot. The outward protrusion may include a plurality of contact points operable to contact to a plurality of positions of the predetermined region of the foot when the compression garment is in the wrapped position with the foot. The positions may at least include the abductor hallucis and flexor hallucis brevis muscles of the foot; however, other positions are contemplated for use with any of the herein disclosed garments and/or associated pads.

The body portion may include upper and lower edges and may be divided by first and second portions. The first portion may be for receiving the foot, guide sleeve, and/or pad and the second portion for wrapping around the foot once the foot and/or other features of the garment are received by the first portion. The first tensioning band may also be inelastic and the guide sleeve may be elastic.

The body portion may also include a divider end that divides the first and second portions and a wrapped end opposite the divider end. In this respect, the guide sleeve may comprise a flexible member extended about the upper and lower edges of the body portion and/or attached to the body portion between the divider and wrapping ends. The flexible member may also form a flexible opening between the flexible member and body portion, the flexible opening capable of forcibly guiding and precisely positioning the foot to a predetermined arrangement with respect to the pad (e.g. guiding the foot to the receiver associated with the metatarsal head of the pad). At least a portion of the flexible member may also be trimmable so that the flexible member can be customized as biased into a three-dimensional curvature conformable to the foot. The flexible member may attach to the divider end along a predetermined pattern contoured to the foot and be disposed between the upper and lower edges. The flexible member may be formed from first and second bands positioned adjacent to and/or between upper and lower edges of the body portion. The flexible member of the guide sleeve may also be formed from two pieces releasably attached to each other at a central connection.

The pad may also removably disposed between the guide sleeve and the body portion. The guide sleeve can also be releasably attached to the dividing end, the wrapping end, and/or other locations of the body portion. At least one end of the first tensioning band may be releasably attachable to a plurality of locations and orientations on the body portion or itself so that the first tensioning band is adjustable between a plurality of compression levels.

In other embodiments, one or more compression level measuring systems can be used for indicating an actual compression level delivered to the foot by the garment.

An exemplary system can include a system operable to measure indicia of the first tensioning band and/or the body portion when the garment is donned by the foot with a card. The card can include a scale for measuring a separation of at least one indicia to determine an actual compression level to the foot associated with the separation. At least one end of the first tensioning band can be releasably attachable to a plurality of locations and/or orientations on the body portion so that the first tensioning band is adjustable between a plurality of compression levels according to the actual compression level measured by the system. In this embodiment, the indicia may be spaced along the first tensioning band and/or the body portion at predetermined intervals, the indicia being ticks, dots, shapes, symbols, patterns, and/or text.

Another exemplary measuring system can include a multi-layer compression measuring system formed on the first tensioning band and/or the outer surface of the base portion. A stretchable base layer can be included along with an upper layer attached at two spaced-apart locations on top of the stretchable base layer. A visual indicator of the actual compression level can be positioned with the upper or base layers and can be observable when the upper layer is pulled taut. The visual indicator of this system may be indicia on the stretchable base layer such that each of the two spaced-apart locations is adjustable and opposing ends of the upper layer can be aligned with indicia on the stretchable base layer. The upper layer can be rigidly attached to the stretchable base layer at one of the two spaced-apart locations and can be releasably attached to the stretchable base layer at the other of the two spaced-apart locations.

Additionally, a portion of the upper layer can permit external viewing of indicia through a window. A portion of the upper layer may also be transparent or translucent and surrounding portions of the upper layer may be opaque. The visual indicator may also be a plurality of indicia on the stretchable base layer and different indicia may be viewable about an edge of the base layer and/or through the portion of the upper layer for external viewing depending upon an amount of stretch of the base layer. The upper layer of the measurement system may also include a first portion and a second portion attached end-to-end, the first and second portions having different stiffnesses. The first portion of the upper layer may be attached to a first location of the stretchable base layer and the second portion of the upper layer may be attached to a second location of the stretchable base layer. The first portion of the upper layer may also be inelastic and the second portion of the upper layer may be elastic, and/or wherein the first and second portions of the upper layer stretch together as the stretchable base layer stretches underneath.

The visual indicator of this system may also include three-dimensional arrangements of the particular feature. For example, if the multi-layer system is installed on the first tensioning band, if the upper layer of the system is pulled flat or otherwise arranged, this can indicate a pre-determined compression level.

The garment may also include additional tensioning bands operatively coupled to the outer surface of the body portion, each of the additional tensioning bands extending away from a lateral edge of the body portion and operable to secure together the first and second portions of the body portion. The bands may extend from the same edge or may extend from both lateral edges. At least one of the bands may also include a cut away portion permitting the at least one of the tensioning bands to be individualized to correspond to a circumference of the foot. The tensioning bands may also be juxtaposingly oriented with respect to each other when operatively coupled to the body portion as well as when arranged wrapped around the foot, pad, and the foot. At least one end of each tensioning band may be releasably attachable to a plurality of locations and orientations on the body portion, itself, or another of the plurality of bands so that the each tensioning band is adjustable between a plurality of compression levels.

In other embodiments, additional tensioning bands may be included and each form part of a pair of tensioning bands extending between opposing lateral edges of the body portion. One of each pair may include a guide or a ring for receiving the other of the pair to secure each of the first and second portions so that the one of each pair is pullable through the ring to adjust inwardly applied tension of the pair of tensioning bands. At least one of each pair of tensioning bands may include a fastener for releasable attachment onto itself and/or onto the outer surface of the body portion.

In other embodiments, an inflatable chamber may be operatively coupled between the body portion and the guide sleeve and in communication with a pressure adjustment mechanism, the inflatable chamber being operable to regulate compression levels delivered to the foot by the garment. The inflatable chamber can be formed by a separate bladder or can also be formed between the guide sleeve and the body portion.

In other embodiments, a heel fastener can be attached to the body portion for securing the garment to a heel of the foot. The pad can also be constructed with a predetermined stiffness for deforming a predetermined amount when a foot is situated thereon in a predetermined arrangement.

In other embodiments, a molded pad for restless leg syndrome is provided, the pad a base with a protrusion comprising a receiver for the metatarsal head and a plurality of contact points operable to apply contact to a plurality of positions of a foot. At least two of the positions contacted by the contact points can include the abductor hallucis and flexor hallucis brevis muscles of the foot. The herein the molded pad can be constructed with a predetermined stiffness for deforming a predetermined amount when a foot is situated thereon in a predetermined arrangement.

The base of the molded pad can be substantially rectangular and the protrusion can extend outwardly with first and second planar portions each having respective heights. The second height can be greater than the first height and the second portion can include the contact points. The first and second planar portions can also be substantially planar with the base. In this regard, the second planar portion can include a first elongate member normal to a second elongate member, the first elongate member being longer than the second elongate member. The first and second planar portions can also have different material stiffnesses and/or the first and second elongate members of the second portion can also have different material stiffnesses. A contoured receiver for the metatarsal head of the foot can be formed at a vertex between the first and second elongate members. A notch can also be disposed adjacent the vertex and the contoured receiver, the notch being recessed into or raised upward from the second planar portion. The molded pad can also have a predetermined material density and/or a distinct density for each contact point. The base of the molded pad can also be formed with a shoe, a shoe insert, or a gel pad.

In other embodiments, a method of treating restless leg syndrome with a compression garment is disclosed including the following steps: selectively positioning a guide sleeve of the compression garment on an inner surface of a body portion of the compression garment, the guide sleeve having an opening and being dimensioned to wrap together with the body portion around a foot; selectively positioning a pad of the compression garment between the guide sleeve and the body portion in a predetermined position, the pad comprising an outward protrusion with a plurality of contacts; the guide sleeve guiding the foot through the opening in a predetermined arrangement with the foot; the contacts of the outward protrusion contacting a plurality of positions of the predetermined region of the foot, at least two of the positions including the abductor hallucis and flexor hallucis brevis muscles of the foot; wrapping the body portion around the foot; and tensioning the compression garment to a predetermined compression level applied to the foot by operatively coupling opposing ends of a first tensioning band to locations of an outer surface of the body portion.

The method can also include measuring the predetermined compression level with any of the herein disclosed measuring systems, for example, by measuring separation of indicia of the first tensioning band and/or the body portion when the tensioning band is tensioned with a card, the card comprising a scale for measuring separation and correlating the separation to a measured compression level; and adjusting the predetermined compression level by repositioning at least one end of the first tensioning band onto the body portion according to the measured compression level.

In other embodiments, a system for monitoring compression levels and biometric data of a user is provided including any of the previously described garments. A plurality of sensors (including pressure sensors, strain gauges, etc.) can be attached to the body portion and/or the first tensioning band, each sensor operable to measure compression data between the garment and the foot. A biometric sensor can be removably attached to the user and capable of measuring biometric data regarding the user such as heart rate, motion state, pressure of the user's skin, etc. A computing device can be operatively connected to each sensor, the computing device comprising a processor, memory, a user interface for receiving input from the user and a display medium, the computing device operable to receive data from each sensor and execute control logic for the sensors.

The control logic can include the following steps: (a) receiving data from each sensor, wherein data from the biometric sensor at least provides data regarding biometric sensed data and wherein data from the sensors of the garment provides real-time compression levels of respective locations of each pressure sensor on the garment; (b) analyzing data from the sensors of the garment to determine a respective inwardly applied compression level delivered by the garment to the foot; (c) analyzing data from the sensors of the garment of (b) and the biometric sensor to determine whether inwardly applied compression level of each location associated with each pressure sensor requires adjusting; and (d) manually and/or automatically adjusting tension levels in one or all respective locations the sensors of the garment (e.g. actuating servos, motors, TENS units, etc of the garment).

The control logic can also include: (e) determining whether a change in data from one or more the sensors of the garment and/or the biometric sensor exceeds one or more predetermined thresholds; and (f) intermittently broadcasting a notification signal to the computing device wirelessly connected to the sensors if the change in data is determined to exceed the one or more predetermined thresholds. The thresholds can include at least one of the following in connection with the user: a threshold duration of treatment time, a threshold number of treatment sessions in across one or more days, a threshold rest period in between treatment sessions, a threshold number of steps taken across the one or more days, and/or a threshold heart rate. One or more networks can also be included in the system across which the computing device is connectable with one or more servers.

In this respect, the control logic can also include (g) establishing a wireless communication link between the one or more servers and the computing device and transmitting data received from the sensors to the one or more servers.

In other embodiments, the control logic can include: (h) synchronizing a database of user information related to biometric and compression level data resident to the one or more servers; and (i) using the database of user information to control the computing device and/or the sensors of the garment via visual, auditory, and/or haptic output received by the user interface of the computing device and/or the sensors, the computing device being a mobile device. The mobile device can include a software application with access to the control logic, the software application of the mobile device comprising the following management capabilities: continuously monitoring data of the sensors; configuring alert message parameters for transmitting one or more alert messages and recipients of the one or more alert messages; controlling one or more parameters of the sensors of the garment including minimum thresholds; and/or activating one or more alarm conditions of the sensors.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 3A is an upper perspective view of an exemplary garment showing the pad positioned with the garment without an exemplary guide sleeve.

FIG. 3B is an upper perspective view of an exemplary garment showing the pad positioned with the garment with an exemplary guide sleeve.

FIG. 11 depicts an embodiment of the garment of FIG. 5 with exemplary tensioning bands from opposing sides of the garment.

DETAILED DESCRIPTION

Figure 1:
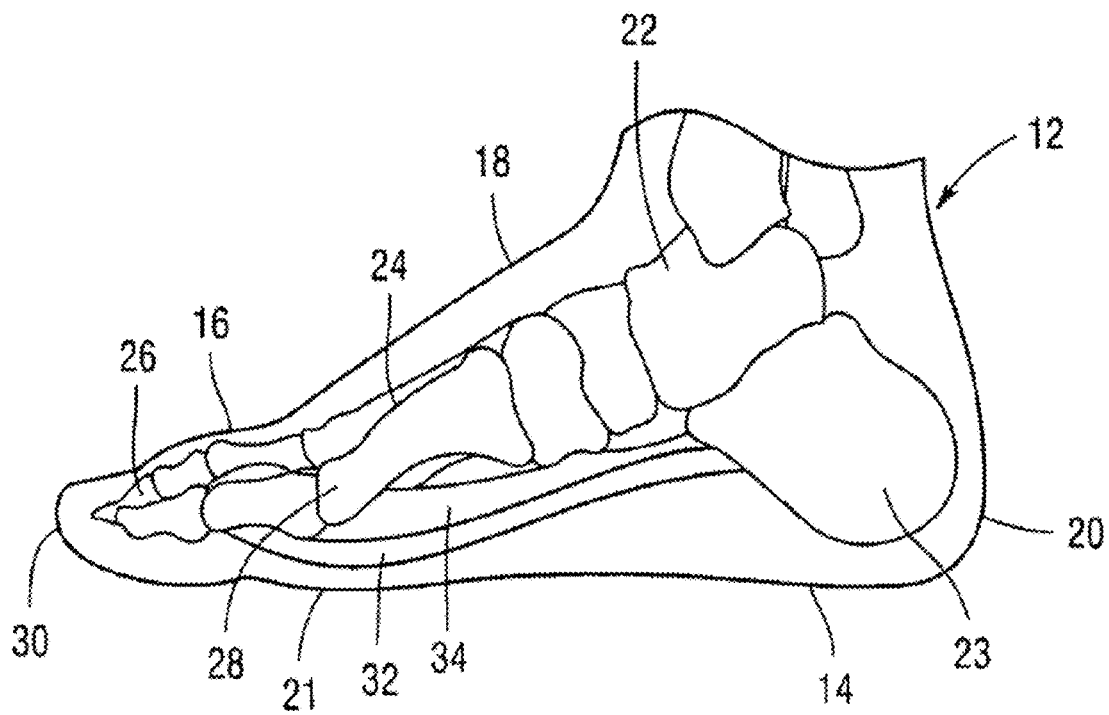
FIG. 1 is a side elevational view illustrating features of the human foot.

To facilitate an understanding of the principals and features of the disclosed technology, illustrative embodiments are explained above. The components described hereinafter as making up various elements of the disclosed technology are intended to be illustrative and not restrictive. Many suitable components that would perform the same or similar functions as components described herein are intended to be embraced within the scope of the disclosed electronic devices and methods. Such other components not described herein may include, but are not limited to, for example, components developed after development of the disclosed technology.

It must also be noted that, as used in the specification and the appended claims, the singular forms "a," "an" and "the" include plural referents unless the context clearly dictates otherwise. By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, garments donned by a "subject", "individual", or "patient" may be a human or any animal with a foot. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may also be any applicable human patient, for example.

Compression devices can be wraps that tighten through one or more fasteners and/or can be tightened with one or more bands, fasteners, or the like to deliver the desired compression to a particular limb. Adjusting and/or fastening one or more bands of a particular garment can require pulling or pushing on free ends of the bands (or any fasteners of the bands) for attachment. A user may have to maneuver free ends of the band which can require a skill as well as strength. Persons suffering from neurological conditions, including RLS, may struggle to adequately adjust the respective band and/or have sufficient capability to both precisely position their limb with a garment and then have sufficient force to move a tightening band to the necessary location for adequate compression.

The herein disclosed garment resolves these and other problems of the art by providing a compression garment for use with a foot with a foot-positioning sleeve removably or integrally attached to the garment and one or more bands for delivering compression to the foot and maintaining the foot in an aligned position with the garment. The herein disclosed garment and its constituent features create for an easy yet reliable and precise garment for use to treatment of one or more neurological disorders including RLS.

In establishing certain engineering principles, it is understood that when wrapping a band around a limb including foot 12, the pressure under the band (compression) is related to the force applied to the band (tension) and the circumference of the material being wrapped, according to the following equation derived from Laplace's Law: $P=2\pi F/CW$, wherein P is pressure, F is force in the form of tension in the band, C is circumference; and W is the width of the band.

The force F is assumed here to be parallel to the circumference of foot 12 and thus perpendicular to the longitudinal axis or distal-proximal direction of foot 12. However, force F need not have that exact direction as long as it has a component in the circumferential direction. If a portion of the band is elastic, the stretch of the elastic is related to the force, according to the following equation: $S=FL/WY$, wherein S is stretch (change in length), L is length, and Y is a constant for a band of given thickness and composition. Force F and stretch S for a particular fabric can be determined empirically, by applying different forces F to samples of the material, and charting stretch S as a function of force F.

With this in mind, the herein disclosed garment is operable to be donned by a foot and have one or more tensioning bands and/or wraps tightened to impart an inwardly applied compression force to one or more locations of a user's foot 12 for resolving and/or managing certain neurological afflictions including restless leg syndrome (RLS). As previously discussed, RLS is an affliction of the lower extremities whose symptoms often manifest themselves with twitching and consequent muscle soreness of the leg and foot. Prior approaches to RLS have included pharmaceutical treatments as well as certain exercises to relieve and alleviate symptoms.

Figure 2:
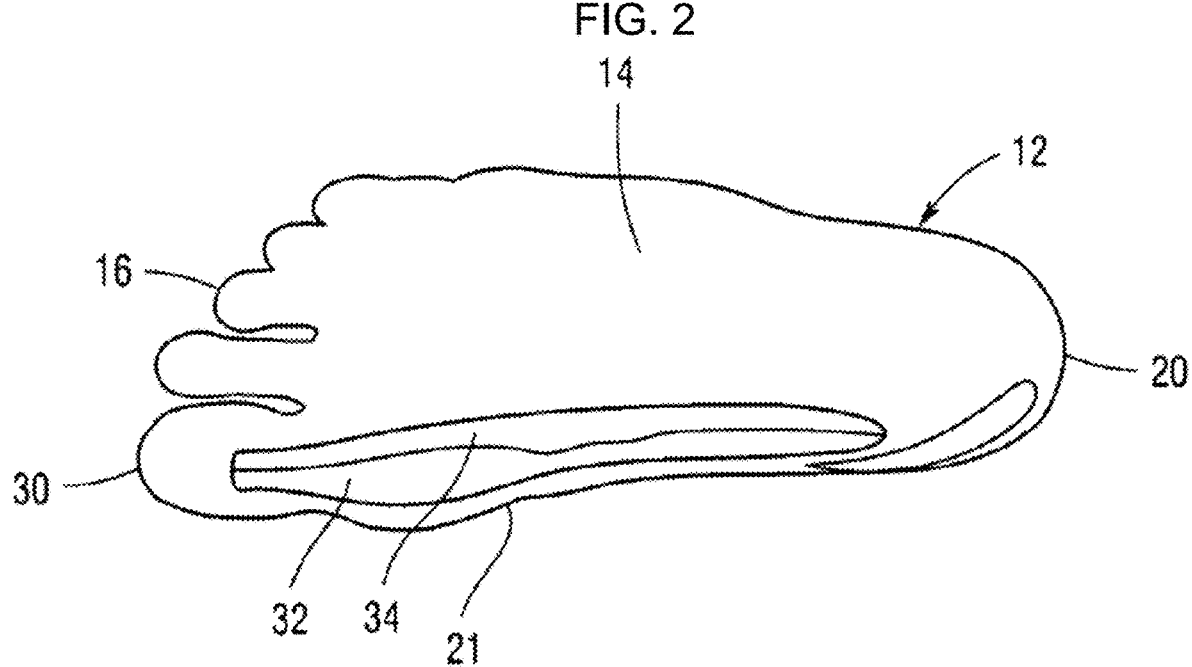
FIG. 2 is a bottom plan view of the foot of FIG. 1.

The herein disclosed garment can be unobtrusively worn on the individual's foot for applying pressure over extended periods of time and can be easily and precisely positioned and also be adjusted according a specific individual's treatment regimen in all manners of situations including standing, sitting, and/or in a supine position. In this regard, FIGS. 1 and 2 depict a representative foot 12 that includes a sole 14, toes 16, a foot upper side 18, a heel 20, and an inner side 21. Prominent bones of foot 12 are also shown including the talus 22, the calcaneus 23, the metatarsals 24, the phalanges 26 and the metatarsal head 28 that is the bony prominence immediately behind the big toe 30. Muscles of foot 12 to which the present garment 10 may be connected includes the medial, plantar and lateral edge of the flexor hallucis brevis muscle 32 and the abductor hallucis muscles 34.

Illustrated in FIGS. 3-13B is are embodiments of the disclosed compression garment 10 for relieving and alleviating the symptoms associated with one or more neurological afflictions including RLS, restless arms, as well as Plantar Fasciitis, Peripheral Neuropathy, Anxiety Disorder, Attention Deficit Hyperactivity Disorder, Augmentation and Rebound from Dopamine Agonist Therapy, Back Pain and Chronic Back Pain, Dementia, Depression, Dyskinesia, Dystonia, Fibromyalgia, Foot Pain, Inherited Neuropsychiatric Disorder, Mental Depressive Disorder, Metatarsalgia, Multiple Sclerosis, Muscle Cramp Disorder, Muscular Dystrophy, Nocturnal Foot and Leg Cramps, Neuroma, Morton's Neuroma, Plantar Neuroma, Traumatic Neuroma, Parkinson's Disease, Periodic Limb Movement Disorder, Peripheral Nerve Disorder, Plantar Fasciitis, Obsessive Compulsive Disorder, Radiculopathy, Sacroiliac pain, Tourette Syndrome, as well as circulatory disorders treatable through compression garments. Device 10 may be easy to don and more importantly, be used for precise, reliable, and comfortable positioning with respect to foot 12.

Turning to FIG. 3A is an upper perspective view of an exemplary garment 10 without its corresponding guide sleeve 50. Specifically, device 10 may include a flexible body portion 40 dimensioned and capable of being wrapped about wrapped about and secured to foot 12. It should be noted that garment 10 can be used when sitting down or recumbent but may also be used when a user is in an ambulatory state. Body portion 40 can include a raised portion 48 constructed from a durable material that may be elastic and/or non-elastic along some or all of body portion 40. Body portion 40 may include a uniform thickness or a plurality of regions with selectively positioned varying thicknesses that form a padded portion. For example, body portion 40 may include a perimetral edge portion 48 with a greater thickness than an inner, central portion 44, 46 formed therebetween. Pad 48 may also include one or more laminates from a material such as breathoprene. Body portion 40 may in turn be divided into first 44 and second 46 portions, wherein first portion 44 is capable of receiving a foot engaging pad 60 and second portion 46 is capable of wrapping over pad 60 when positioned with foot 12. In this regard, pad 60 can include specialized foot receivers for precisely and easy positioning of foot 12 with pad 60 including a metatarsal head receiver 67.

Pad 60 of FIG. 3A is shown for use with a right foot 12 and may be uniformly constructed from a material having a predetermined stiffness and/or material density so that when foot 12 is properly positioned thereon, one or more contacts of pad 60 apply contact across a predetermined region and/or one or more positions of foot 12 for resolving the specific neurological disorder. For instance, receiver 67 can include a contoured recess operable to guide metatarsal head 28 into a predetermined engagement with pad 60 so that, for example, an upraised notch 67 operatively communicates with metatarsal head 28 and/or the flexor hallucis brevis muscle 30. Receiver 67 may include a recess of pad 60 selectively removed to facilitate this precise engagement. Pad 60 may also include a hook section with a loop section on the interior portion of sleeve 50 and/or first portion 44. This ensures that pad 60 is precisely and easily positioned prior to, during, and/or after use. Other securement and/or anti-migration mechanisms may be used to fix pad 60 to sleeve 50 and/or first portion 44 including but not limited to magnetic fasteners, chemical adhesion, mechanical fasteners and/or surface treatments (e.g. a textured surface, a surface with one or more bumps or grooves that induce friction between pad 60 and first portion 44, etc.). It is to be understood that any of the foregoing features including members 64 and 66 and/or notch 65 may be recesses or inward protrusions and yet achieve similar results as the depicted members 64, 66 and/or notch 65.

Pad 60 is therefore provided with first portion 44 for precise, selective, and controlled application of contact between selected locations of foot 12 and pad 60. As shown in FIG. 3A, pad 60 may include a first planar section 62 that is substantially raised from base 69 of pad 60. One or more second portions may rise from section 62 and be oriented substantially planar with section 62 and base 69 of pad 60. For instance, an elongate stem member 66 may be centrally positioned and extend upward from section 62, wherein member 66 may be aligned parallel with upper and lower edges of body portion 40. In contrast, a perpendicularly oriented member 64 may be provided adjacent an inner sole 14 of foot 12 and is planar with and normal to member 66. In those embodiments where members 64 and 66 are joined, metatarsal head receiver 67 may be etched into a joint formed between members 64 and 66. Additionally, a notch 65 may be positioned adjacent to or nearby receiver 67. Notch 65 may preferably be a contoured recess but may also include one or more outward protrusions. In those embodiments where notch 65 is recessed, flexibility of pad 60 may be improved since material that otherwise builds up in that area is removed. Notch 65 may also facilitate precise positioning with metatarsal head 28 and/or the flexor hallucis brevis muscle 30 with respect to pad 60 when foot 12 is disposed thereon.

In a preferred embodiment, members 64 and 66 may be arranged as a molded T-shaped member. However, pad 60 is not so limited and any shape or number of individually arranged contacts in place of members 64 and 66 as well as receiver 67 and notch 65 may be used as needed or required. It is understood that "T-shaped" as described herein with respect to pad 60 may include any shape, pattern, and/or array of distinct or connected contacts of a pad that may be raised, perpendicularly arranged, and/or recessed in a manner to apply contact the a desired location or locations of foot 12, including the hallucis brevis 32 and abductor hallucis muscles 34.

Pad 60 may also be a molded, uniform block with a raised T-shaped portion formed by distinct density changes within the uniform block with a predetermined variance in pressure caused by distinct density changes as between two or more portions of pad 60. Pad 60 in this embodiment is not so limited, however, and other differences between two or more portions of pad 60 are contemplated including material types, mechanical differences, and/or matter state as between solid, gas, liquid (e.g. fillable bladders), etc. Pad 60 may also be trimmable as needed or required by foot 12 as well as included one or more visual indicators indicating information such as locations thereon for use with foot 12. Pad 60 may also include indicia such as material stiffnesses and/or densities of locations of pad 60.

Pad 60 may also have points that are perpendicularly-arranged or in an intersecting pattern but also be disconnected in a plurality of individual contacts. While pad 60 may have a predetermined density, pad 60 may also utilize different materials with differing densities (e.g. multiple foams with different densities) in a manner that selectively targets regions of high and low pressure. For example, member 64 may have somewhat softer than member 66, or vice versa. Pad 60 may therefore be injection molded and may include ergonomics such as notch 65 or receiver 67 operable to intelligently locate pad 60 on foot 12 and/or utilize selectively positioned softer regions of pad 60 for added comfort while donned. Preferably, pad 60 may be constructed from closed cell foam to keep pad 60 from flattening and respond to force applied thereon by foot 12 and garment 10 with increasing resistance.

Pad 60 can also be formed from, or enclosed by, one or more laminates such that a selectively designed three dimensional structure can be individualized for incorporation into garment 10 itself such that garment 10 and pad 60 are formed as a single unit. Alternatively, instead of being a wrapping compression garment, garment 10 may instead be formed as a shoe insert or sole. In this regard, pad 60 could also be formed integrally with one or more laminates that precisely position pad 60 thereon for use and insert into a shoe of a user. Pad 60 may also be incorporated into a molded shoe design, a foot bath, an adaptor for use with a chair, and an adaptor for use in bed. Pad 60 may also be incorporated into a pad formed of a gel as well as a thermal molded pad capable of being formed to a specific foot 12 of the user. Optionally, any of the herein disclosed garments, including garment 10 when as a shoe insert, molded shoed, gel pad, or heat molded pad, may include a heel securement band for further securement to foot 12. Pad 60 may also be formed from a fillable skin with one or more of members 64, 66, notch 65, and receiver 67. In this embodiment, pad 60 may be filled from one or more granules or particulates include foam chips.

Turning to FIG. 3B, a guide sleeve 50 is now shown assembled with garment 10 and substantially covering pad 60 that is depicted disposed between sleeve 50 and first portion 44. A chamber may be defined between sleeve 50 and first portion 44 that with an opening 54 disposed along a lower edge of first portion 44 sized to receive pad 60 and/or foot 12. Other openings may also be included as needed or required. In this regard, sleeve 50 may be formed from one or multiple flexible members with a predetermined elasticity and/or power. Sleeve 50 may be include a predetermined amount of elongation and/or a predetermined force required for sleeve 50 to be stretched to its predetermined amount of elongation. Opening 54 of sleeve 50 may be defined by an attachment adjacent or near a dividing end 56 that divides portions 44 and 46. Opening 54 of sleeve 50 may be also defined at an opposing end 52 opposite end 56, wherein either attachments at ends 52 and 56 can be removable to accommodate different sized feet 12. Additionally, either edge of sleeve 50 that is attached to first portion 44 can be adjusted, trimmed, and/or repositioned as needed or required to accommodate different sized feet 12 as well as varying levels of compression that may be required for a particular condition.

When guide sleeve 50 is assembled with first portion 44, pad 60 may be removably disposed between sleeve 50. Advantageously, opening 54 of sleeve 50 may be capable of forcibly guiding foot 12 therethrough so that foot 12 can only be arranged with respect to pad 60, first portion 44, and sleeve 50 in one arrangement. This ensures that certain features of foot 12 communicate and contact certain features of pad 60 only so that desired pressure is delivered between by garment 10 to foot 12 for user-specific treatment. For example, sleeve 50 may precisely guide foot 12 so that members 64, 66, receiver 67, and/or notch 65 abutting and only applying pressure to muscles 32, 34 in the precise orientation for treatment. In this regard, sleeve 50 may also protect a user from injury or misuse of garment 10 with pad 60 by ensuring that precise positioning and mating between foot 12 and garment 10 is achieved. Sleeve 50 may therefore include one or more padded portions to protection foot 12 from tensioning bands 72 wrapped thereabout and/or any fasteners used to secure garment 10 in a wrapped state.

As can also be seen in FIGS. 3A and 3B, one or more tensioning bands 72 may extend from a lateral side edge for securing second portion 46 with first portion 44 when pad 60 and corresponding sleeve 54 are assembled thereon. Band 72 may be an elongate member that is inelastic and/or elastic with one or more fasteners 75 positioned on or adjacent a distal end 77 opposite the respective edge of body portion 40 from which band 72 extends. Fasteners 75 may be fixedly attached (e.g. sonic welded, sewn or glued) or may be removably attachable to the desired position of band 72. Preferably, each band 72 is attached at a first location on an outer surface 13 of garment 10 and then is capable of causing second portion 46 to fold over onto portion 44 until be secured onto itself, another band 72, or another location of an outer surface 13 of garment 10 through fastener 75. Body portion 40 may also include secondary fasteners and/or closure systems for quick fitting that operate independent of and/or in concert with fastener 75. For example, fastener 75 of band 72 may be tightened to the appropriate tension level and instead a zipper may then be used to don garment 10 to foot 12 for quick fitting and repeated tension.

Advantageously, and as shown below, tension in bands 72 may be both easily monitored and adjustable so that corresponding compression applied by garment 10 to specified locations of foot 12, including muscles 32 and 34, is precisely controlled according to a patient's treatment protocol.

Figure 4:
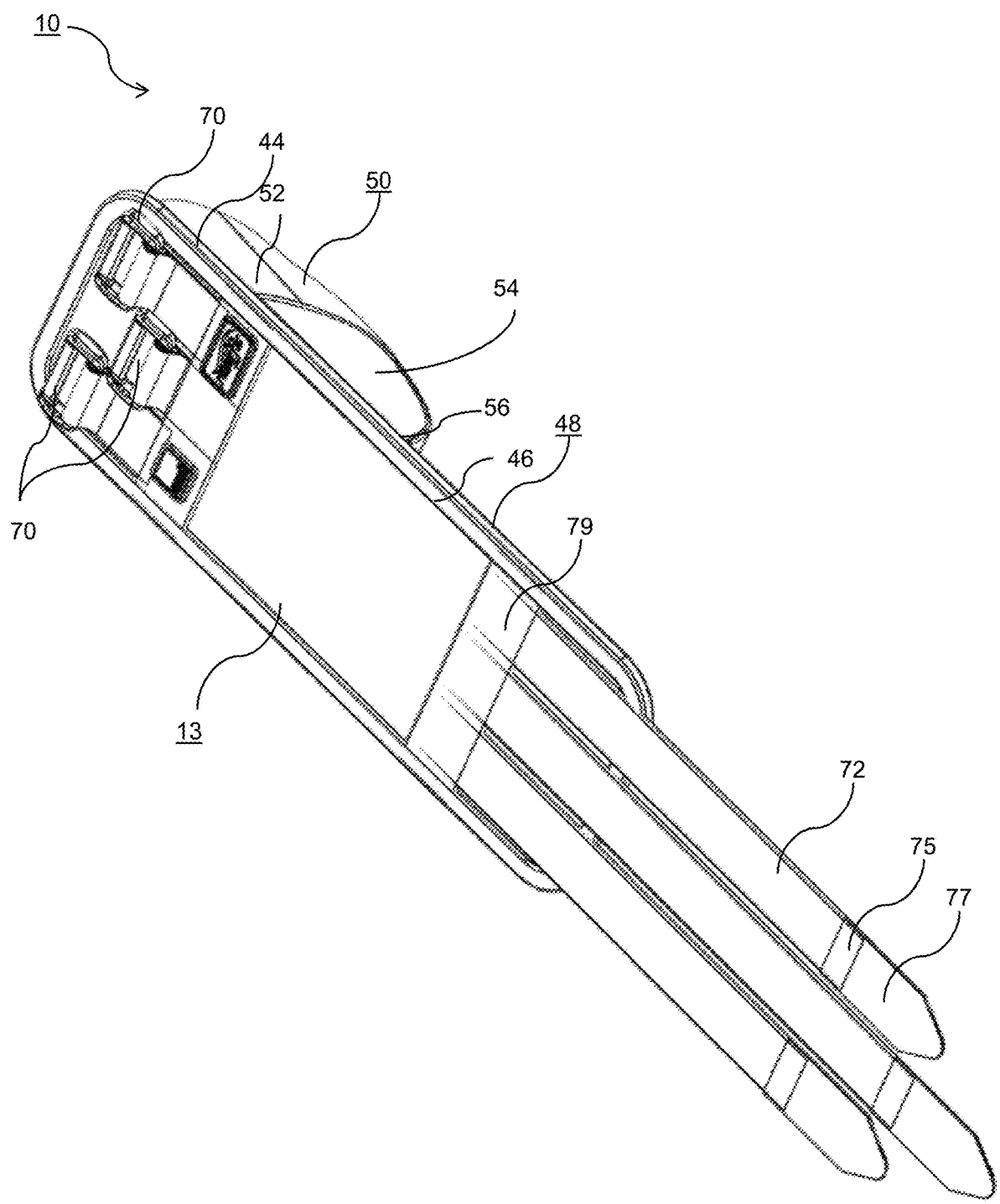
FIG. 4 is a lower perspective view of an exemplary garment.

Turning to FIG. 4 is a lower perspective view of garment 10 showing its outer surface 13 and one or more bands 72 extending from a lateral side edge opposite sleeve 50. It is to be understood that garment 10 is not limited and any number of bands 72 can be used with garment 10 and can extend from any edge or location of garment 10 as needed or required. In the embodiment of FIG. 4, bands 72 can be seen attached to garment respective proximal ends 79 and disposed to move second portion 46 to wrap about pad 60 and sleeve 50 until being secured thereon. As shown, distal end 77 of each band 72 can be cause second portion 46 to pivot towards first portion 44 until being inserted through corresponding guide rings 70. End 77 may then be pulled back onto itself, one of the other bands 72, or attached to any location of garment 10 via fastener 75 when a desired tension of band 72 is obtained.

Each band 72 can be trimmable and each end 79 of band 72 may be fixedly attached or may b removably attached for added adjustability of selective compression to one or more desired contact areas of foot 12 as between garment 10, pad 60 and bands 72 (e.g. one area of foot 12 can receive more compression than another area of foot 12).

Figure 5:
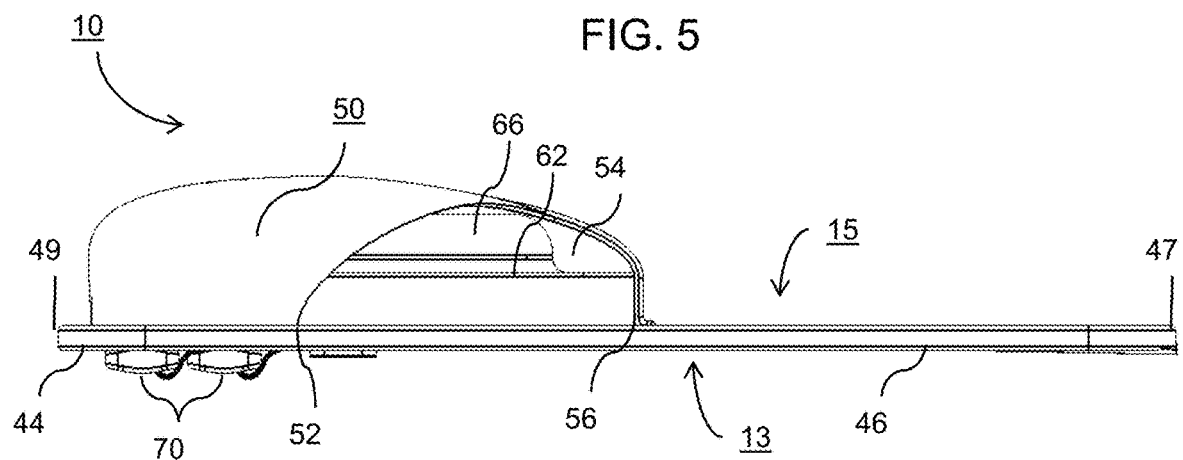
FIG. 5 depicts a side plan view of an exemplary garment without the one or more tensioning bands.
Figure 6:
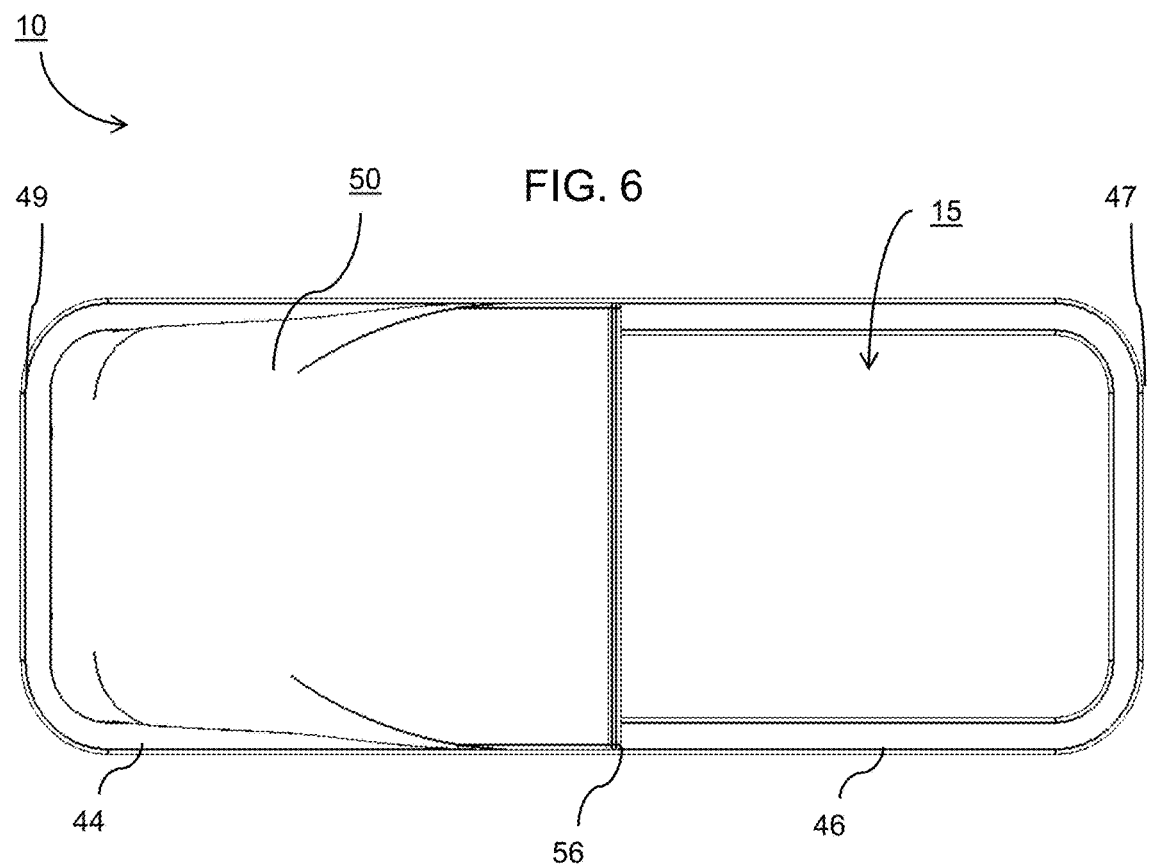
FIG. 6 depicts a top plan view of the garment of FIG. 5.

Turning to FIG. 5 is a side plan view of garment 10 without one or more bands 72. FIG. 6 is a top plan view of garment 10 similarly without one or more bands 72. As previously shown, guide sleeve 50 may be attached about first portion 44 at least between ends 52 and 56 to form an opening 54. In FIG. 5 specifically, an exemplary opening 54 is shown where pad 60 and corresponding member 66 and surface 62 can be seen operable to receive right foot 12. Sleeve is shown clearly positioned in first portion 44 adjacent edge 49 whereas opposing edge 47 can be seen operable to wrap over towards 49 to secure second portion 46 to guide sleeve, 50, pad 60, and ultimately first portion 44. Underneath sleeve 50 on the opposite outer surface 13 of garment are also the previously described rings 70 positioned to receive bands 72 when attached to garment 10 as previously described. However, garment 10 is also contemplated for use without any bands 72 and thus without rings 70. Instead, one or more fasteners can be positioned on second portion 46 operable to be removably attached onto outer surface 13 of first portion 44.

Figure 7:
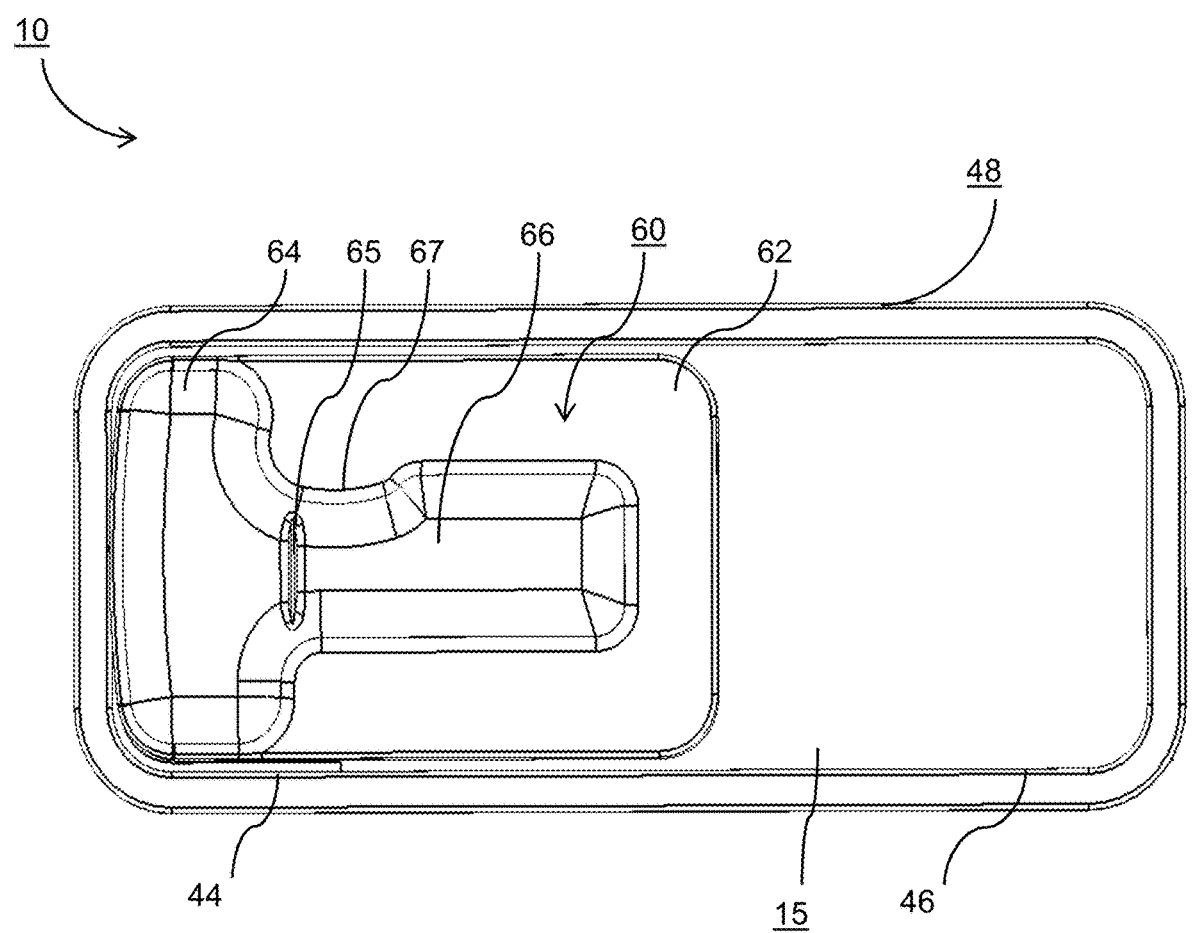
FIG. 7 depicts a top plan view of the garment of FIG. 5 with the guide sleeve removed for viewing an exemplary pad of the garment.

Turning to FIG. 7 is a top plan view of garment 10 without sleeve 50 and one or more bands 72. Instead, an exemplary pad 60 can be seen with members 66 and 64 perpendicularly arranged on surface 62. Receiver 67 can be seen as a curved recess or indentation abuttingly engaged where members 64 and 66 are joined, wherein receiver 67 may be designed to receive metatarsal head 28 during positioning of foot 12 thereon. Notch 65 can also be seen adjacent receiver 67 and substantially aligned with member 64 and thus normal to member 66. It is to be understood that any or all features of pad 60 can be formed together as shown or may be independent, disconnected features. In either respect, pad 60 comprises a plurality of selectively positioned contacts operable to easily and precisely align with foot and selectively contact one or more locations of foot 12 including, for example, muscles 32 and 34. As previously described, pad 60 may have the same stiffness and density throughout or may be constructed from varying stiffness and density levels as needed or required.

Figure 8A:
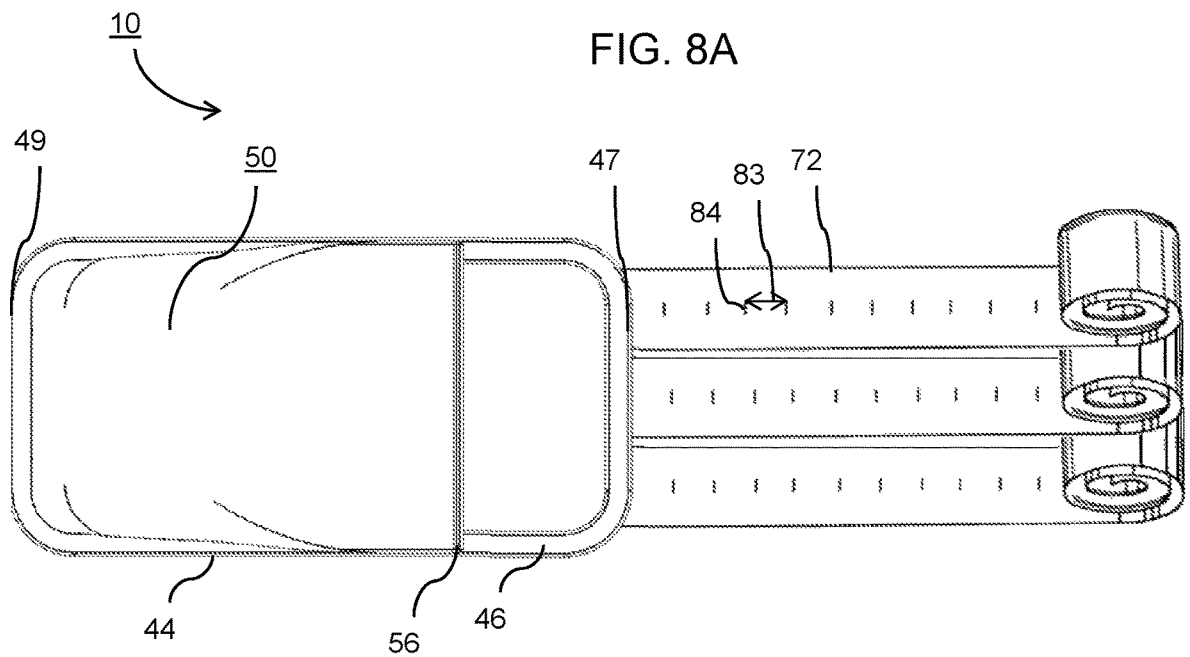
FIG. 8A depicts an embodiment of the garment of FIG. 5 with an exemplary compression measuring system that includes indicia on exemplary tensioning bands.

FIG. 8A shows an exemplary compression garment 10 including bands 72. Each band 72 may be elastic or substantially elastic along its length or longitudinal axis. In the embodiments of FIG. 8A, bands 72 may therefore be elastic or substantially elastic along the axis along which tension is to be applied. Each band 72 may alternatively be elastic along only a part of its length.

Each band 72 may have visual indicators such as indicia 84 printed along its elastic length, or elastic axis, spaced by intervals 83. Each interval 83 may have a fixed or specified length when respective band 72 is not under tension. Each of bands 72 may be pulled under tension around foot 12 at a selected location, attached to itself via guide rings 70, and/or attachable to other portions of garment 10, using a fastener 75 and thus applying compression to that portion of foot 12 as well as maintaining the precise contact between foot 12 and pad 60.

As can be seen, indicia 84 may include one or more tick marks spaced along band 72 at intervals 83. However, indicia 84 is not so limited and could include dots, geometric shapes, symbols, patterns, text, or the like spaced at intervals 83 therealong for measurement with the referenced measuring device such as a calibrated scale or card upon donning of each band 72 to foot 12 and/or later stretching of each band 72. Each interval 83 may be spaced at a predetermined distance from each other when the bands 72 are unstretched. In contrast, when a band 72 is under tension, the spacing between each indicia 84 may serve to accurately measure compression delivered by garment 10 to foot 12 at one or more multiple locations.

For example, an interval 83 between successive indicia 84 may increase when band 72 is under tension and lengthens. The distance between successive indicia 84 may then be measured after application of garment 10 to foot 12, wherein the measured distance may indicate tension in band 72 and in turn the specific amount of compression applied by garment 10 to foot 12.

Figure 8B:
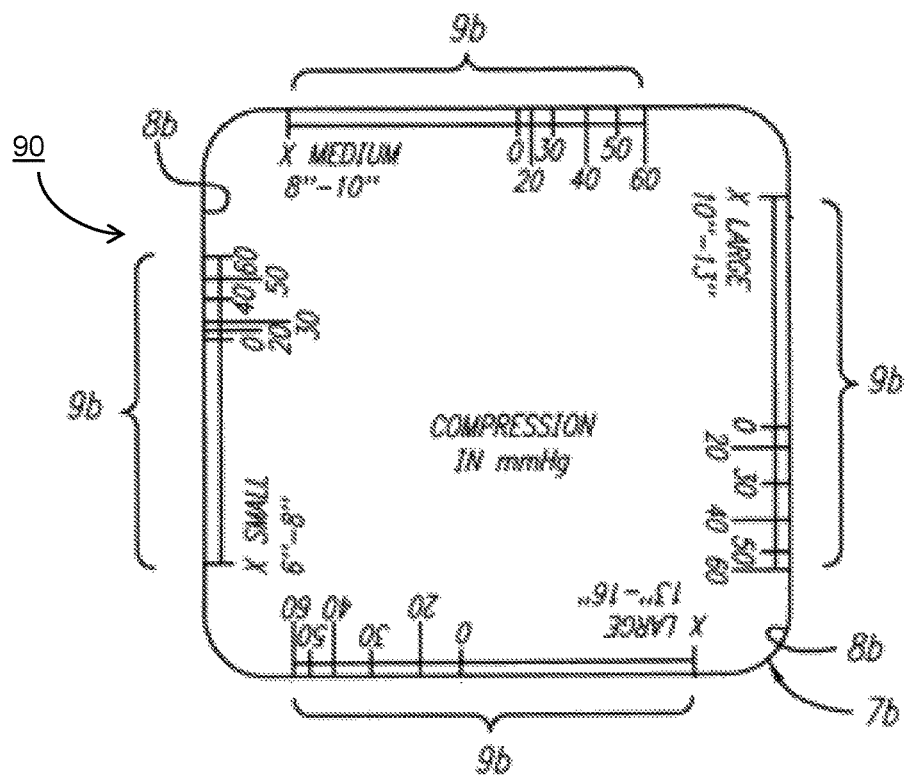
FIG. 8B depicts is a view of a measuring card for determining compression levels of the garment in FIG. 8A.

Systems of measuring compression levels and/or tension associated with bands 72 and garment 10 are also contemplated such as using the card 90 shown in FIG. 8B. Card 90 may be used to determine tension at multiple locations of band 72 as well as multiple locations about foot 12 when assembled with garment 10. After measuring, band 72 can optionally be removed, relocated, and/or adjusted by releasing fastener 75, selectively positioning said fastener 75, and re-fastening fastener 75 to the selected location and/or desired tension. Card 90 may include reference numerals 7b disposed adjacent a plurality of edges 8b with measurement scales 9b calibrated to measure the distance between indicia 84 in the bands 72.

Figure 9A:
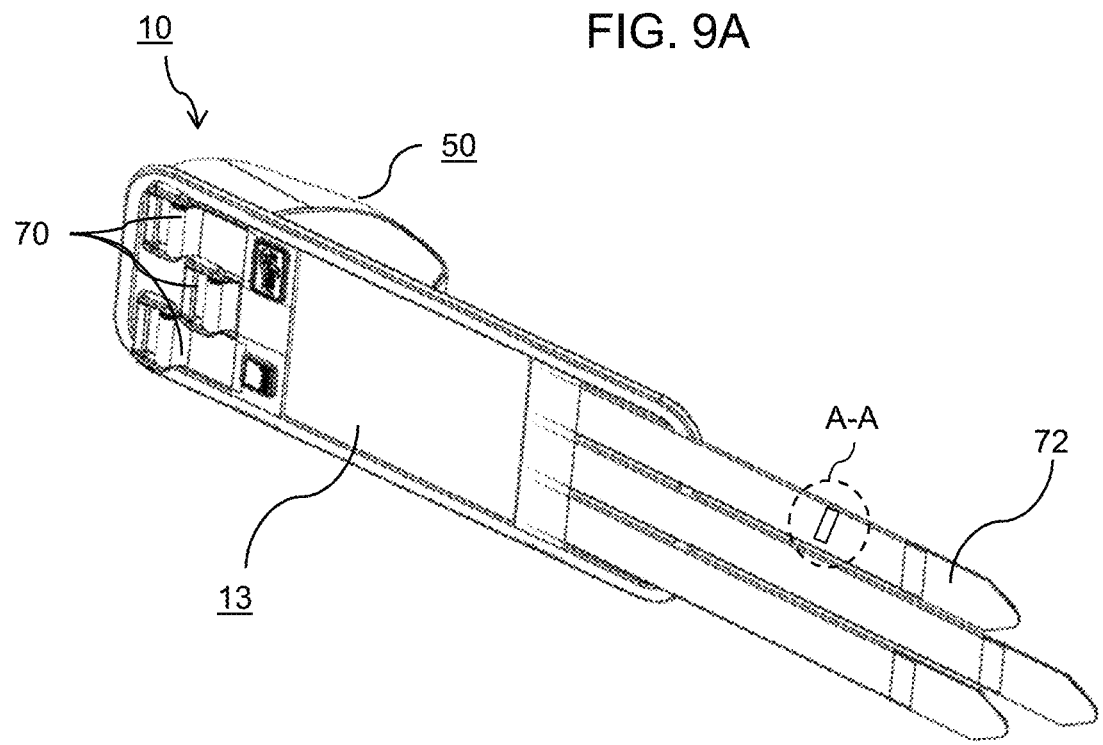
FIG. 9A depicts an embodiment of the garment of FIG. 5 with an exemplary multi-layer compression measuring system.
Figure 9B:
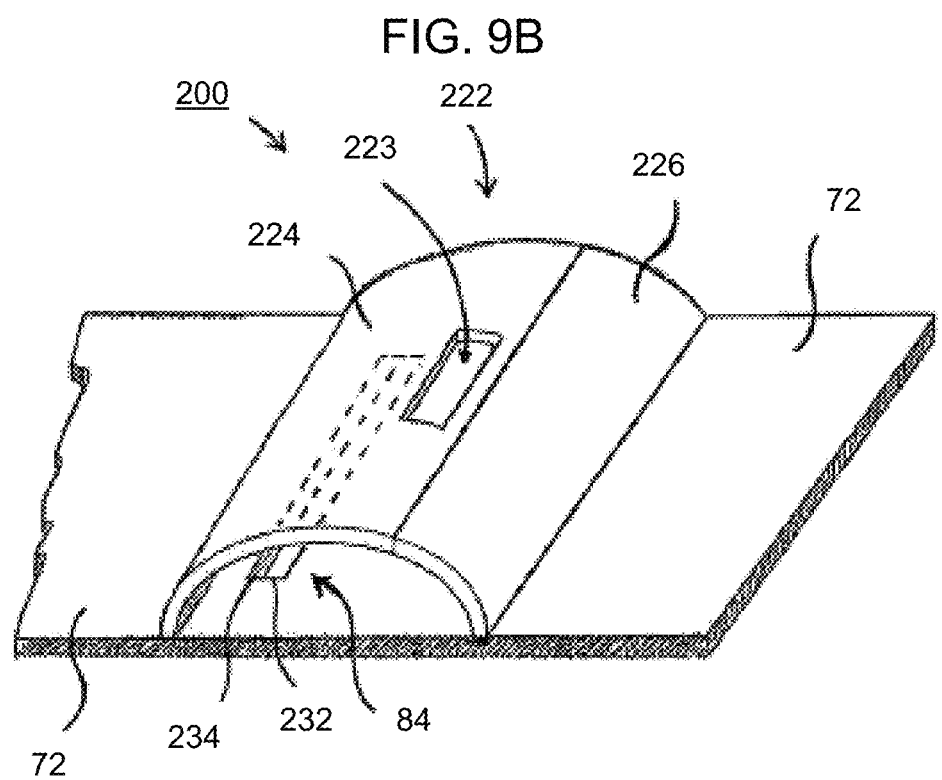
FIG. 9B depicts a close up view of plane A-A of FIG. 9A with an exemplary multi-layered compression measuring system in one of the bands prior to stretching.

FIGS. 9A through 9B show certain non-limiting embodiments of a multi-layer compression measurement system 200 for use with one or more of bands 72 and/or any portion of body portion 40. System 200 can be installed in one or more bands 72 of the garment as shown in FIGS. 9A through 9B but can be incorporated in any portion of garment 10 including portions of body portion 40 and/or sleeve 50.

FIG. 9B is a perspective view of system 200 including a stretchable base layer 221 having indicia 84 thereon; and a stretchable upper layer 222 positioned on top of the stretchable base layer. Importantly, stretchable upper layer 222 comprises a first portion 224 and a second portion 226 joined end-to-end. Importantly as well, first portion 224 and second portion 226 can have different stiffnesses. For example, first portion 224 may be inelastic and second portion 226 may be elastic. One end of first portion 224 is attached (e.g.: sewn) to base layer 221 and one end of second portion 226 is also attached (e.g.: sewn) to base layer 221, as illustrated. The other ends of first and second portions 224 and 226 are also attached (e.g.: sewn) together, as also illustrated.

It is to be understood that either or both of the two layers in system 200 may in turn be made of two, three or more layers or sections connected together, and therefore any references in the specification and claims to two layers refer to at least two layers, each made of one, two, three or more layers or sections connected together. Additionally, indicia 84 may be positioned on system 200 by being printed, painted, glued, sewn onto or otherwise attached to the upper surface of base layer 221. In one preferred embodiment, indicia 84 comprise marking 232 and a red marking 234. In other preferred embodiments, the indicia may comprise a tension force scale calibrated to display different tension levels. In operation, indicia 84 can be seen by a user through window 223 in first portion 224 of top layer 222.

Figure 10A:
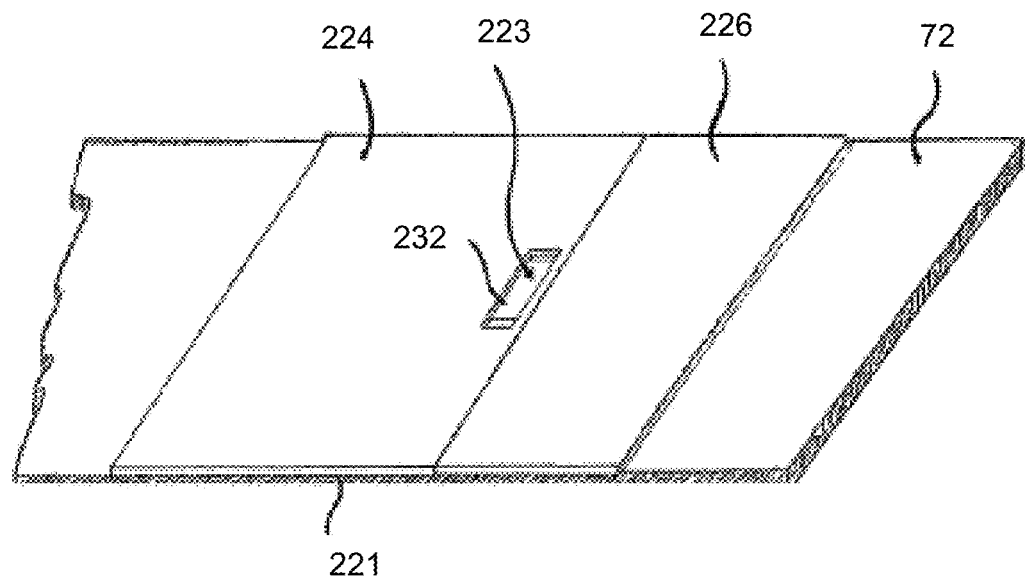
FIG. 10A is a perspective view of the measurement system of FIG. 9B with a predetermined tension applied to the band.
Figure 10B:
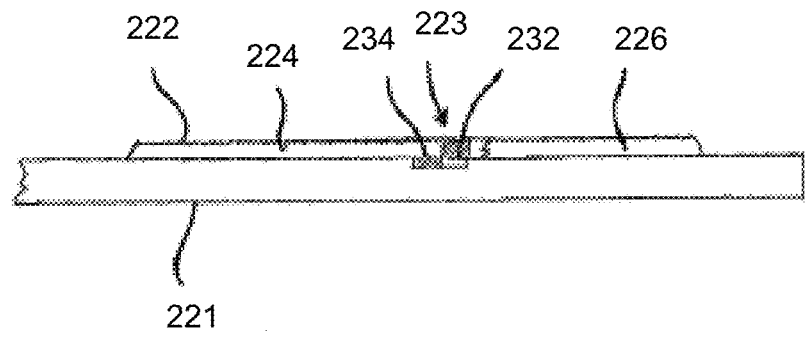
FIG. 10B is a sectional side elevation view corresponding to FIG. 10A.

FIGS. 10A and 10B show a predetermined tension applied to measurement system 200 so that indicia 84 is viewable through window 223. However, visual indicators of system 200 may not only be colors, notches, letters or numbers and instead may be shape or arrangement that the particular feature of system 200 is in. For example, when respective band 72 having system 200 is in a flattened state, this state may indicate that a predetermined amount of tension is being delivered to garment 10 that corresponds to a particular level of compression.

Additionally, the base and upper layers may be made of differing material properties including differing stiffnesses. As a result, one of the layers may stretch more than the other. This can result in what appears to the user as a relative movement of the window or transparent/translucent layer with respect to the indicia on the base layer underneath that stretches less.

Other measurement systems are also contemplated for use with the herein disclosed garment including an inflatable bladder or chamber formed between garment 10 and foot 12 that is attached to a pneumatic fluid pressure regulating mechanism. The bladder may inflate with fluids such as liquids or gas, manually or automatically (e.g. with servos, small motors, memory alloy materials, embedded electrodes, transcutaneous electrical nerve stimulation (TENS or TNS) devices, etc.), according to need or preference. In addition, any of the foregoing garments can be used in conjunction with hot and/or cold thermal therapies. Other measurement and control systems are discussed more particularly below.

FIG. 11 shows another exemplary compression garment 10 capable of wrapping around foot 12. Specifically, FIG. 11 shows a top plan view of garment 10 in an exploded state with removably attachable bands, prior to be assembled together and donned by foot 12 of a user. Bands 72 may attach to body portion 40 and/or extend from either side of body portion 40. Each releasably attachable band 72 of FIG. 11 can be positioned at different locations and/or orientations on body portion 40, itself, or other of bands 72.

Optionally, bands 72 of FIG. 11 may have loops or pockets such as guide rings 70 of FIG. 3 to aid with fastening and tensioning of bands 72. Each rings 70 may also be releasably attachable to a plurality of locations and arrangement on body portion 40 as needed or required. Bands 72 can also be made of different materials having different stretch characteristics.

For example, bands 72 can also be made of decreasing power moving from big toe 30 towards heel 20 of foot 12 so that if all bands 72 were wrapped around foot 12, the band 72 with more power would apply more compression. Any number of bands 72 can be used as needed or required and bands 72 may also be juxtaposingly engaged when bands 72 are attached and garment 10 is wrapped around foot 12 in use. One or more of the lateral edges of body portion 40 may also include a trimmable portion with or without sizing indicia that can be trimmed to fit and/or to a predetermined curve that depends on the shape and size of a particular foot 12. Together with the material properties of each band 72, including elasticity and/or inelasticity, desired tensioning angles at which each band is under tension during use can be tailored for each user and a particular condition.

Furthermore, a band with known material properties (e.g. stiffness) can be chosen such that the compression level beneath the garment is known when the band is applied with just enough tension to completely elongate the material (e.g. 20-30 mmHg, 30-40 mmHg, etc.) In optional embodiments, all or portions of garment 10 may be made of active textiles (i.e.: that change heat, electricity, etc.), or be inflatable, or made of a disposable material impregnated with pharmaceuticals, antimicrobials, or the like.

Figure 12:
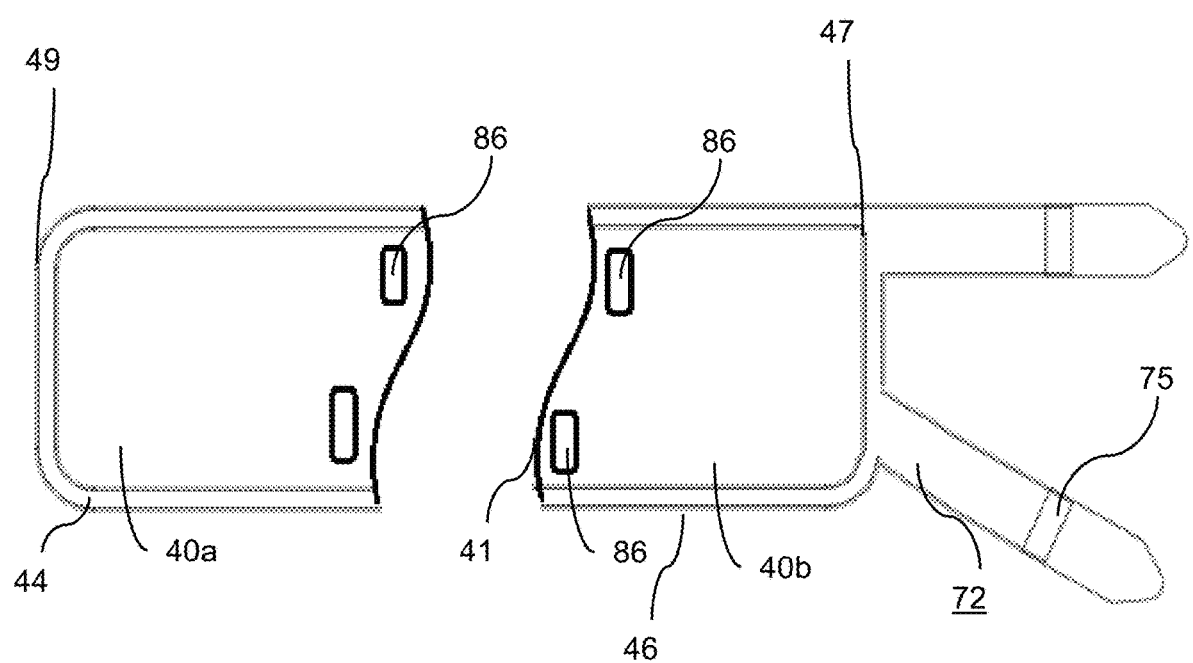
FIG. 12 is top plan view of another exemplary compression garment for a foot having a multi-part body portion and integrally formed tensioning bands extending from a lateral edge.

Turning to FIG. 12, another embodiment of garment 10 can be seen for one-size-fits-all compression garment easily and quickly customizable to match the circumference profile of foot 12. Garment 10 in this respect may include a multi-part body portion 40 comprising first 40a and second portions 40b releasably attachable to each other. A plurality of bands 72 are seen extending from portion 40b, releasably or integrally, from one of its sides as shown. Bands 72 in turn may be fastened onto opposing portion 40b, be juxtaposed between other bands 72, and/or extend circumferentially around foot 12 and back onto their own portions respectively.

Portions 40b and/or 40a may also have fasteners 86 disposed along inner edge 41 that can be curved. Fasteners 86 of either edge 41 can be spaced allowing portions 40a and 40b to take a three dimensional contoured shape and conform to foot 12. It is understood that sleeve 50 can be arranged and positioned on either portions 40a and 40b so that similarly, foot 12 can be easily and precisely positioned with pad 60, sleeve 50 and corresponding bands 72 to the desired position and/or tension.

Figure 13A:
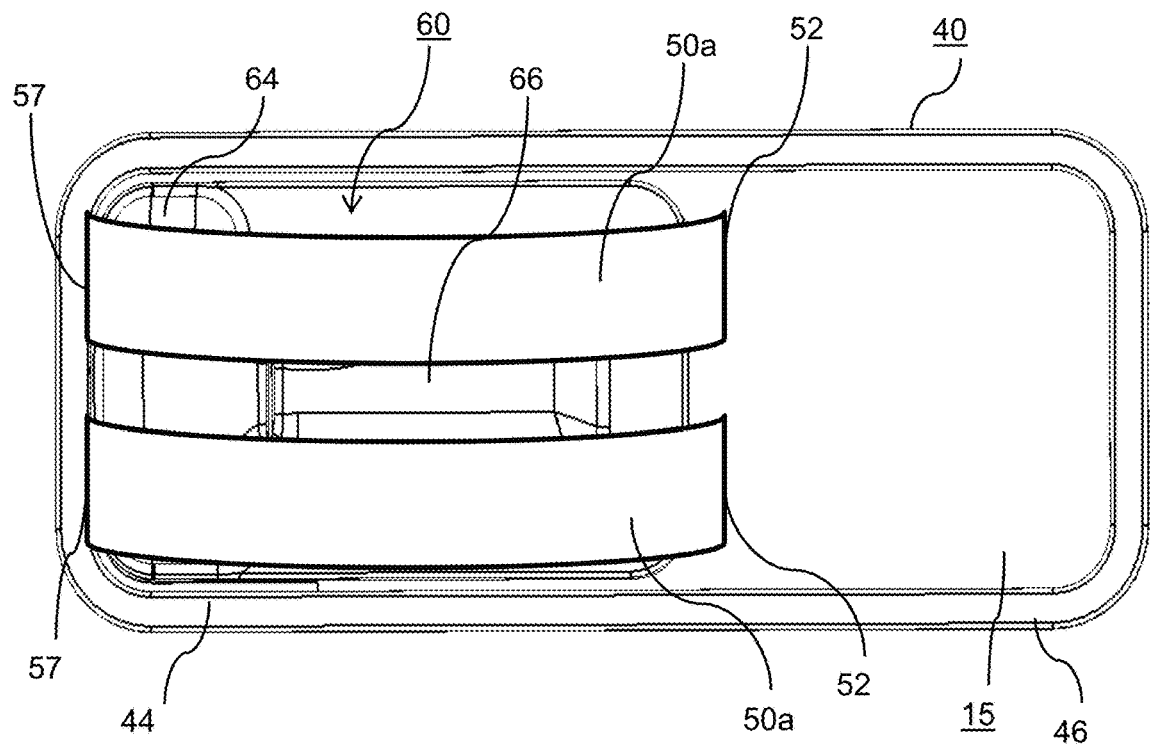
FIG. 13A is a top plan view an alternative embodiment with a guide sleeve system formed from a pair of parallel guide bands.
Figure 13B:
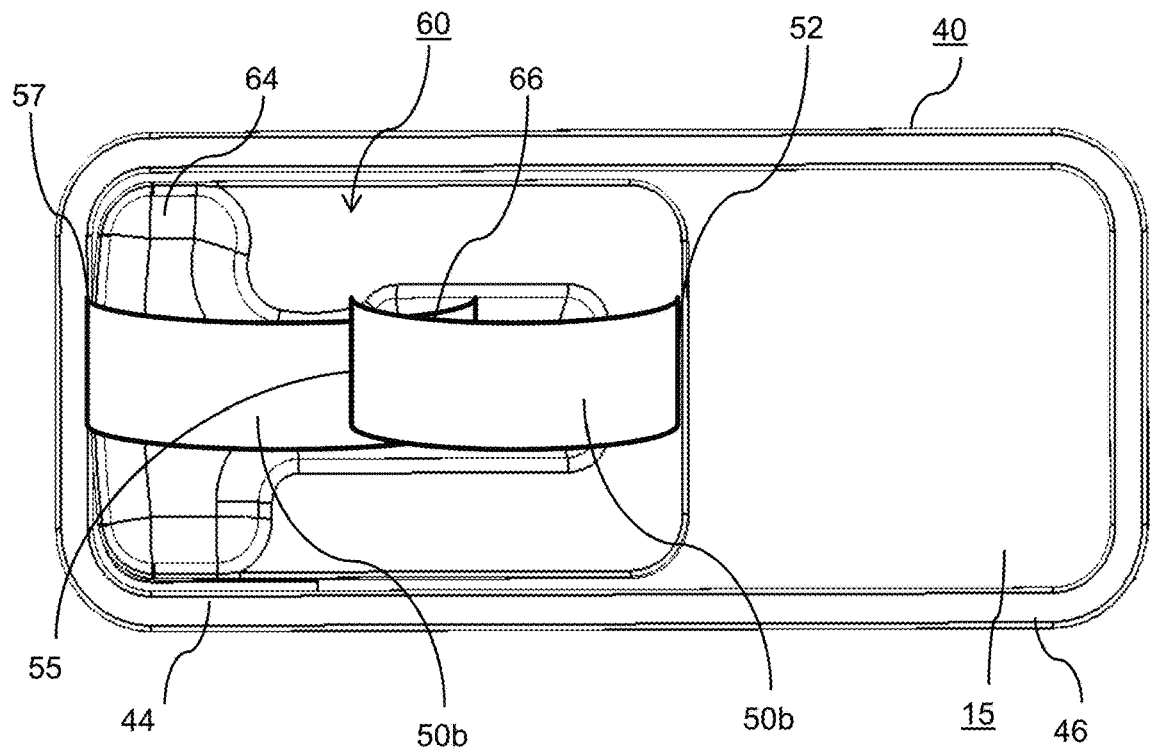
FIG. 13B is a top plan view of another alternative embodiment with a guide sleeve formed from a single band.

FIGS. 13A and 13B show guide sleeve systems for use with the herein disclosed garment 10 having one or more guide bands 50a, 50b that are capable of wrapping together about pad 60 as well as foot 12 prior to bands 72 wrapping garment 10 being in a wrapped state with foot 12. Bands 50a, 50b may have a fixed end 52 and a free end 57. Fixed end 52 can be attached (e.g.: sewn or glued) to body portion 40 whereas free end 57 can be releasably attached to body portion 40 by fasteners such as hook and loop fasteners and is thus positionable at a plurality of locations on portion 40. Additionally, as seen in FIG. 13B, each of bands 50b can be attached to each other at respective opposing free fasteners 55 of each free end. Guide bands 50a, 50b can be used as a multi-part sleeve capable of precisely, comfortably, and easily positioning foot 12 with respective portions of garment 10 and pad 60 to safely and non-invasively treat any of the forgoing neurological disorders, including RLS.

Figure 14:
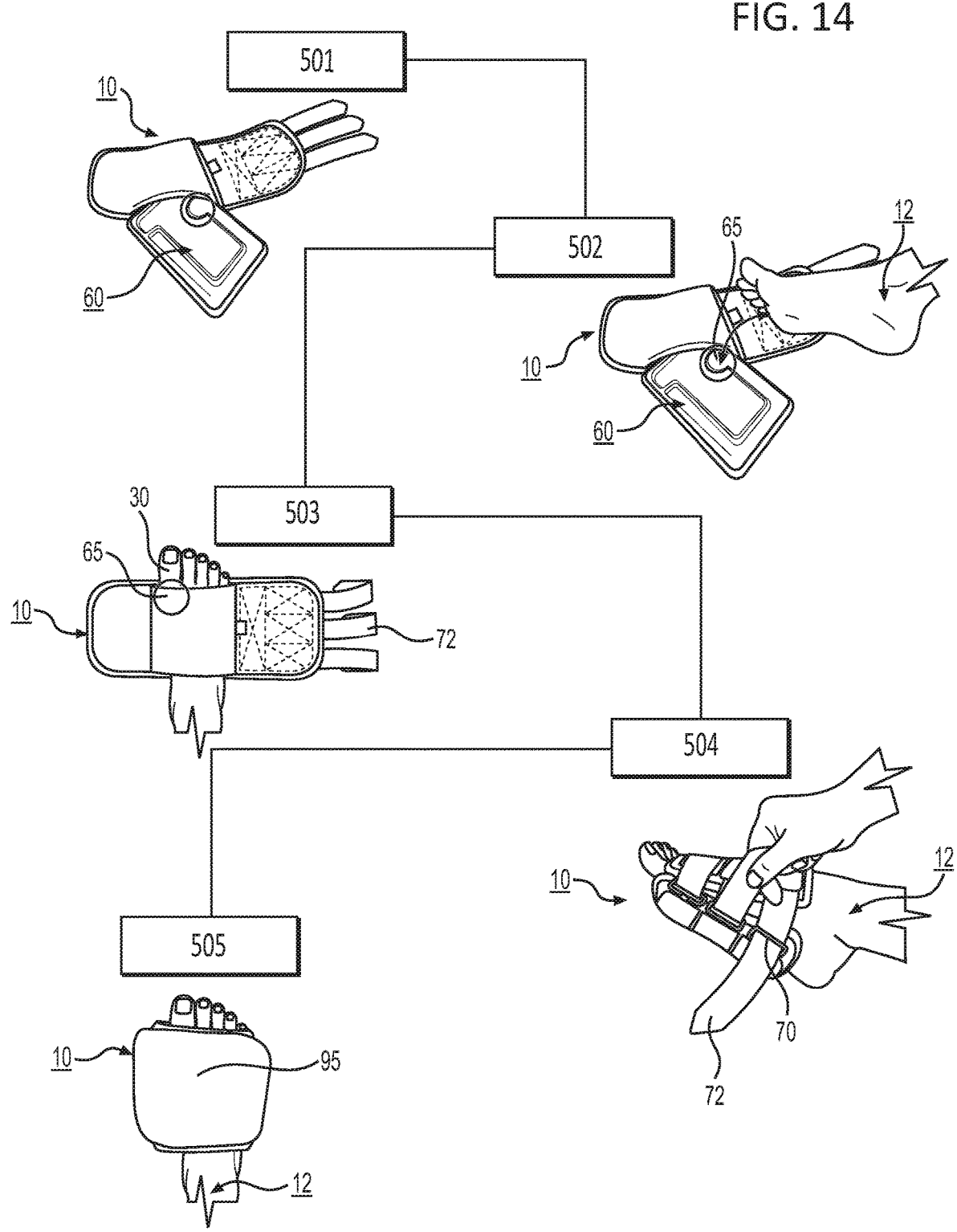
FIG. 14 is a schematic overview of one process of using an exemplary garment.

Any of the herein disclosed garments 10 can be used as shown in the schematic overview of FIG. 14. In step 501, garment 10 may be assembled as desired and then pad 60 oriented with its crosspiece 64 faced forward may be removably inserted through opening 54 of guide sleeve 50. As can be seen, the flexible member of guide sleeve 50 with its predetermined resistance to stretching may both receive pad 60 and forcibly guide it to a predetermined position operably for identifying the region of foot 12 to which pad 60 will contact. In step 502, the base of big toe 30 of foot 12 may identify a base of pad 60 adapted to specifically receive toe 30. In step 503, foot 12 may be slidably inserted through opening 54 and be forcibly guided to the predetermined position with pad 60.

In certain embodiments of this arrangement, the user may be incapable of mislocating or misorienting pad 60 and garment 10 with foot 12 due to the auto-positioning features imparted by pad 60 and/or guide sleeve 50. As can also be seen in step 503, foot 12 and pad 60 have been properly positioned so that contacts of pad 60 are precisely oriented and positioned to the desired positions of foot 12 for treatment of neurological conditions such as RLS. In step 504, bands 70 are secured between portions 44 and 46 of garment 10 to the desired tensioning and corresponding compression. The application of contact between pad 60 and the desired region of foot 12 can later be adjusted, manually and/or automatically, according to need and/or preference.

In step [505], a cover or cover sleeve 95 may optionally be slid over garment 10 now precisely and properly assembled with foot 12 in a wrapped position. One embodiment of a cover 95 may include a shoe tongue design that is capable of encircling oar being wrapped back over bands 72 if long enough to protect foot 12 from bands 72 when secured thereabout. A cover sleeve 95 can also be particularly advantageous for users donning garment 10 at night and/or seeking to avoid entanglement with external objects during use. The cover sleeve 95 when used with garment 10 could offer an additional compression component for foot 12. An arched sleeve could also be provided for use with cover sleeve 95 and/or garment 10 separate from sleeve 95 for additional support to foot 12 and liner protection for sleeve 50 or any herein disclosed component of garment 10.

Figure 15:
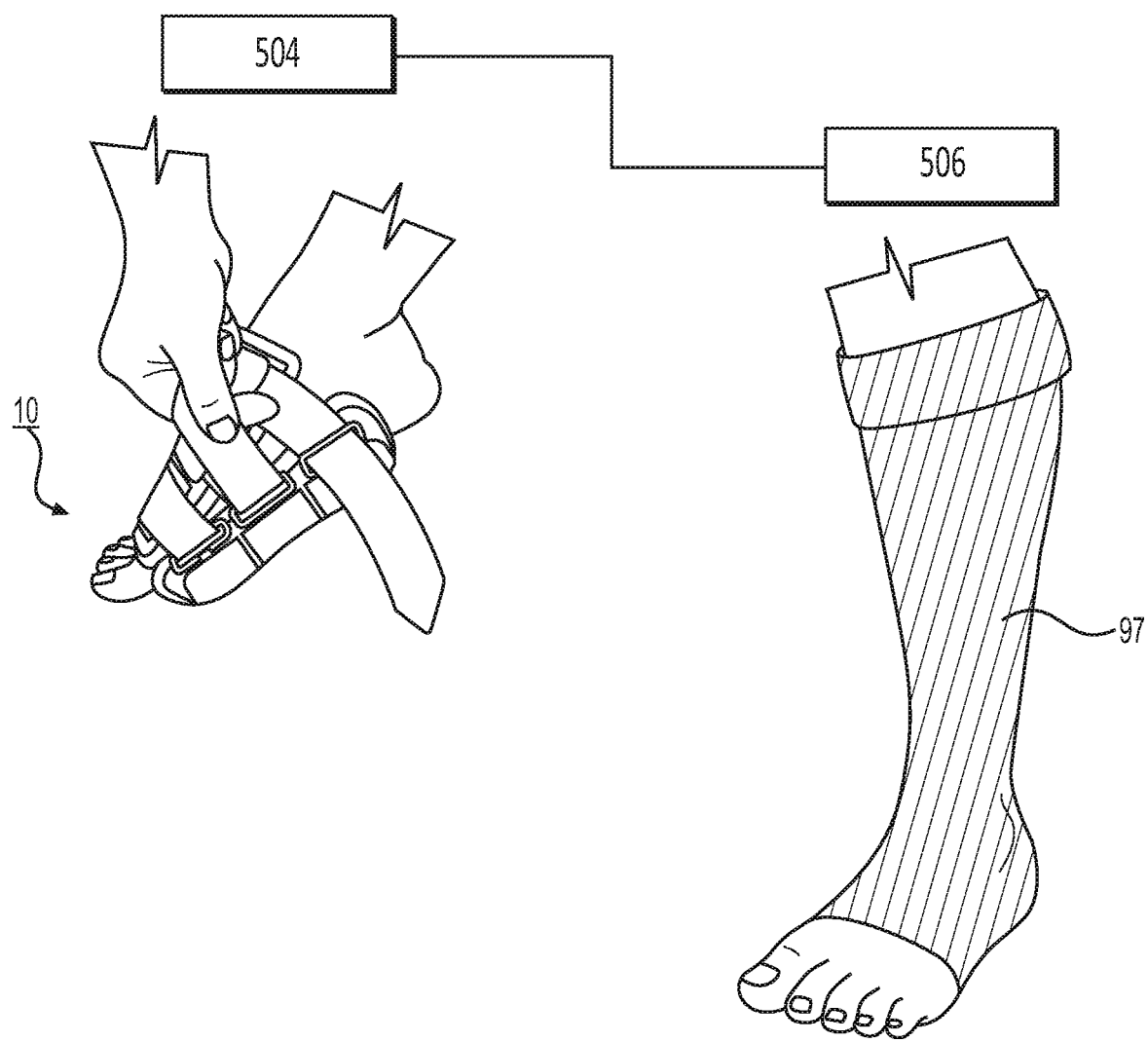
FIG. 15 is a schematic overview of another process using an exemplary garment and compression stocking.

Turning to FIG. 15, in step 506 is similar to step 505 of FIG. 14 wherein compression stocking 97 (e.g. an elastic stocking) is shown having been slid over garment 10 on foot 12, wherein garment 10 can include pad 60, portion 40, sleeve 50, and/or bands 72. Stocking 97 is not so limited and could also be used between garment 10 and foot 12 as well as be integrally formed with pad 60. In this respect, stocking 97 could impart distinct pressure changes around pad 60 as well as provide additional compression component to foot 12 (and/or limbs thereabout) so that a compression profile of stocking 97 could be varied. Accordingly, a different pressure can be applied over pad 60 of garment 10 and also continued on foot 12 or surrounding limbs for other disorders such as lymphedema, venous disease, or the like.

In certain embodiments, stocking 97 may be both circular and flat knit based on the use of elastic fibers such as spandex or latex. Elastic fiber of the stocking 97 may be permit the stocking 97 to provide compression to foot 12 as well as surrounding limbs and also to stretch in order to apply the stocking 97 to foot 12 and surrounding limbs. An exemplary stocking 97 as shown in FIG. 15 may also provide a consistent or static compression to foot 12 and/or surrounding limbs. In this respect, when an individual changes position such as supine to standing, a respective limb circumference can change. The stocking 97 can then stretch to accommodate the change in circumference and maintains a fairly consistent compression level regardless of position or movement to foot 12.

The compression profile of stocking 97 could be varied in such a way that different pressure are applied over the pad and also continued on the limb for other disorders (lymphedema, venous disease, etc.). Stocking 97 can also be easy to put on and its compression level fluctuation range can be adjusted to a new range level per the user's preference to increase or decrease working pressure and compression level fluctuation range in a particular region of foot 12 and/or any surrounding limbs.

Any of the herein disclosed garments 10 can be operatively connected to one or more tension sensors as well as one or more biometric sensors and/or motion sensors in connection with the user to further assess both real-time compression levels being delivered to the user as well as one or more biometric conditions of the user. Notably, tension sensors such as strain gauges and/or pressure sensors may be operable to detect compression levels of garment 10 and biometric and motions sensors may be capable of detecting data such as motion conditions of the user, and/or desired physiological conditions of the user. Each sensor may be directly incorporated in the garment 10 and/or coupled to the user directly and (for example, physically, electrically and/or optically coupled, including wired and/or wirelessly couplings with garment 10 and/or the user).

One or more sensors may be coupled to the user to provide data which is representative of the physiological condition of the user (e.g. heart rate) and/or a particular tension in at a particular location of garment 10 needs to be adjusted. Motion sensors operable to be attached to the user contemplated for use with the herein disclosed garment 10 can include an accelerometer, pedometer, gyroscopes, piezofilms, contact switches and/or all combinations thereof. The output data of these one or more sensors can be analyzed to assess a motion state of the user when donning garment 10. Indeed, all types of sensors and sensing techniques, including known methodologies of inertial sensing, whether now known or later developed, that generate motion state data are contemplated for use with the herein disclosed garment 10 and corresponding system.

Garment 10 can also be in operative communication with a computing device having processing circuitry capable of correlating data from the sensors of garment 10 and/or coupled to the user to detect actual, real-time compression levels to determine a particular compression level that should be used according to the user's specific needs. For example, if the one or more physiological sensors detect that a user is sitting, standing, lying down, etc, and the user's heart rate is at a predetermined level, then the system may determine that a certain level of compression at a predetermined location is necessary. Optionally, garment 10 may have electrodes embedded therein, include servos, small motors, actuators, actuator materials, and/or TENS units in communication with the tension sensors capable of automatically adjusting tension levels of the bands once fastened by a user. Optionally, one or more massage implements and/or vibration mechanisms may be incorporated with the herein disclosed system, including directly in garment 10 or elsewhere on the user, wherein the massage implements and vibration mechanisms can be capable of also being monitored and/or controlled manually or automatically, as needed or required.

One or more computing devices, including a mobile device (e.g. a smart phone or a tablet) and a personal computer, can be used and operatively connected with any of the foregoing sensors to detect compression levels delivered by the garment 10 to foot 12, detect other health conditions of the user, use this information to determine user-specific compression required for a user, as well as automatically and/or manually control compression between the garment and foot 12.

In this regard, one or more sensors may be affixed to the user during, prior to, and/or after operation. Attachment mechanisms may be included such as hook and loop fasteners, clips, straps, or the like to facilitate easy coupling of the one or more sensors to the user and/or garment 10. The processing circuitry of system 300 may be operably to receive, store, and/or analyze information detected from the one or more sensors as well as utilize discrete or integrated control logic, and/or one or more state machines, processors (suitably programmed) and/or field programmable gate arrays (or combinations thereof). Any circuitry now known or later developed may be employed to calculate, determine, assess, estimate and/or determine the compression levels being delivered to foot by garment 10 as well as modifications to suggested compression levels to the user based on sensor data related to health and/or motion state information of the user. Applications, routines or programs associated with the one or more computing devices and/or sensors coupled to the user and/or garment 10 can be implemented by the processing circuitry using any programming language whether now known or later developed.

For example, an application ("app") on a computing device such as a laptop and/or mobile device be used with garment 10, sensors of garment, sensors coupled to user, and/or constituent features connected therewith. In one embodiment, an app installed on the user's smart phone can track real-time compression levels, compare and analyze these levels with a user's past treatment history database, monitor health conditions of the user, as well as monitor a user's motion. The app may also include display interface logic to interface with the processor of the computing device to display metric information as well as execute alarm management logic to provide a user capability of establishing and/or managing parameters for compression levels and related treatment settings.

The alarm management logic can interface with a timekeeping module (e.g., clock, calendar, time zone, etc.), and can trigger the activation of a particular alarm or required compression levels (e.g. at night time or while a user is sleeping) and the alarm can be in the form of an audible alarm or a non-audible alarm. The computing device and garment 10 may also communicate wirelessly through a radio signal, including across a remote network through a server, via a Wi-Fi signal, a Bluetooth signal, a low energy Bluetooth (e.g., LE Bluetooth) signal, or combinations thereof.

It is understood that the computing device and/or sensors of garment 10 may be capable of communicating wirelessly with each other and/or with or through one or more servers via a network. Instructions associated with any of the herein disclosed measurement systems and/or apps can be downloaded from a server or locally installed to the computing device. The server can be a specialized server or a general server that provides applications to devices, such as an application store.

The design and functionality described in this application is intended to be exemplary in nature and is not intended to limit the instant disclosure in any way. Those having ordinary skill in the art will appreciate that the teachings of the disclosure may be implemented in a variety of suitable forms, including those forms disclosed herein and additional forms known to those having ordinary skill in the art.

Any of the herein disclosed compression garments could be used with a single wrap and/or band, a series of independent movable and/or positionable bands, a series of bands attached at a base of the herein disclosed garment, and/or along any portion thereon. Any of the herein disclosed bands may also be divided into sub-bands of elastic and/or inelastic materials and may also have visual indicators positioned thereon. Visual indicators may include tension or pressure indicators as well as indicators relating to donning states such as left, right, properly positioned, etc. Any of the herein disclosed garments can also be used with other conditions (e.g. diabetes) and/or treatment systems (e.g. using means for delivering vibration to one or more limbs of a user).

Additionally, herein disclosed garments, associated bands, and measuring systems can allow the user to accurately and reliably predict and measure compression levels at one or more multiple locations so that users may accurately and reliably apply pre-selected compression levels and/or compression level fluctuations, change the compression levels being applied including without having to remove the garment from the foot and/or re-position the garment at the desired location of the foot. The user may also set a predetermined tension in all parts of the garment in order to create an automatic distal-proximal compression gradient along the foot. Any of the herein disclosed garments, bands, and/or wraps can also include different stiffnesses in two or more portions yielding different pressure dynamics, including elastic and inelastic portions in the respective garment, band, and/or wrap.

As used in this application, certain terms, when used with any of the foregoing computing systems may be intended to include a computer-related entity, such as but not limited to hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device can be a component. One or more components can also reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Certain embodiments of using the herein disclosed garment 10 and corresponding monitoring and control systems have also been described with reference to block and flow diagrams according to example embodiments of the disclosure. It will be understood that other features, steps, and combinations thereof can be implemented by computer-executable program instructions. Likewise, some described process(es) may not necessarily need to be performed in the order presented, or may not necessarily need to be performed at all, according to some embodiments of the disclosure. Additionally, any claimed or described computer-executable program instructions may be loaded onto any computing device including a mobile device, a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks.

These instructions may also be stored in a computer-readable memory that can direct any computing device or other programmable data processing apparatus to function in a particular manner, such that the instructions stored in the computer-readable memory produce an article of manufacture including instruction means that implement one or more functions specified in the flow diagram block or blocks.

While certain embodiments of this disclosure have been described in connection with what is presently considered to be the most practical and various embodiments, it is to be understood that this disclosure is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the technology and also to enable any person skilled in the art to practice certain embodiments of this technology, including making and using any apparatuses or systems and performing any incorporated methods. The patentable scope of certain embodiments of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A compression garment for a neurological disorder, the garment comprising:
   a body portion operable to wrap around a foot;
   a pad operatively coupled to an inner surface of the body portion in a predetermined position, the pad comprising an outward protrusion;
   a stretchable guide sleeve dimensioned to wrap together with the body portion around the foot, the pad being removably retained between the body portion and the guide sleeve; and
   a first tensioning band operatively coupled to first and second locations of an outer surface of the body portion, the first tensioning band operable to secure opposing first and second portions of the inner surface of the body portion in order to secure the outward protrusion of the pad against the foot in the predetermined position.

2. The garment of claim 1, wherein the outward protrusion of the pad comprises a receiver formed for a metatarsal head of the foot, wherein the outward protrusion of the pad is oriented to apply contact across a predetermined region of the foot when the compression garment is in a wrapped position with the foot.

3. The garment of claim 2, wherein the outward protrusion includes a plurality of contact points operable to apply contact to a plurality of positions of the predetermined region of the foot when the compression garment is in the wrapped position with the foot, the positions at least including the abductor hallucis and flexor hallucis brevis muscles of the foot.

4. The garment of claim 1, wherein the body portion comprises upper and lower edges and is divided by first and second portions, the first portion for receiving the foot and the second portion for wrapping around the foot once the foot is received by the first portion; and
wherein the guide sleeve is attached to the first portion of the body portion.

5. The garment of claim 4, wherein the first tensioning band is inelastic and the guide sleeve is elastic.

6. The garment of claim 4, wherein the first tensioning band is inelastic and the guide sleeve is elastic and the body portion comprising a divider end that divides the first and second portions and a wrapped end opposite the divider end on the first portion, wherein the guide sleeve comprises:
a flexible member extended about the upper and lower edges of the first portion of the body portion, the flexible member being attached to the first portion of the body portion between the divider end and the wrapped end;
wherein a flexible opening is formed between the flexible member and body portion, the flexible opening capable of guiding and precisely positioning the foot to a predetermined arrangement with respect to the pad.

7. The garment of claim 6, wherein at least a portion of the flexible member is trimmable so that the flexible member is biased into a three-dimensional curvature conformable to the foot.

8. The garment of claim 6, wherein the outward protrusion of the pad further comprises a plurality of contact points, at least two of the contact points being for the abductor hallucis and the flexor hallucis brevis muscles.

9. The garment of claim 6, wherein the flexible member of the guide sleeve is formed from two pieces releasably attached to each other at a central connection.

10. The garment of claim 1, wherein at least one end of the first tensioning band is releasably attachable to a plurality of locations and orientations on the body portion or itself so that the first tensioning band is adjustable between a plurality of compression levels.

11. The garment of claim 1, further comprising: an inflatable chamber operatively coupled between the body portion and the guide sleeve, the inflatable chamber comprising an externally accessible pressure adjustment mechanism for regulating compression levels delivered to the foot by the garment.

12. The garment of claim 1, wherein the pad is constructed with a predetermined stiffness for deforming a predetermined amount when a foot is situated thereon in a predetermined arrangement.

13. The garment of claim 1, further comprising: a plurality of pressure sensors attached to the body portion and/or the first tensioning band, each sensor operable to measure compression data between the garment and the foot.

14. A compression garment for restless leg syndrome, the garment comprising:
a body portion operable to wrap around a foot;
a pad operatively coupled to an inner surface of the body portion in a predetermined position, the pad being oriented to apply contact across a predetermined region of the foot, the pad further comprising an inward recess having a receiver formed to receive a metatarsal head of the foot and a plurality of contact points to apply contact to at least abductor hallucis and flexor hallucis brevis muscles of the foot;
a stretchable guide sleeve dimensioned to wrap together with the body portion around the foot, the pad being removably retained between the body portion and the guide sleeve; and
a first tensioning band operatively coupled to first and second locations of the body portion, the first tensioning band operable to secure together opposing first and second portions of the inner surface of the body portion in order to secure the inward recess of the pad against the foot in the predetermined position.

15. A compression garment for a neurological disorder, the garment comprising:
a body portion operable to wrap around a foot wherein the body portion comprises upper and lower edges and is divided by first and second portions, the first portion for receiving the foot and the second portion for wrapping around the foot once the foot is received by the first portion, and a divider end that divides the first and second portions and a wrapped end opposite the divider end on the first portion;
a pad operatively coupled to an inner surface of the body portion in a predetermined position, the pad comprising an outward protrusion and disposable between the body portion and a guide sleeve;
the guide sleeve being stretchable and dimensioned to wrap together with the body portion around the foot comprising a flexible member extended about the upper and lower edges of the first portion of the body portion, the flexible member being attached to the first portion of the body portion between the divider end and the wrapped end, wherein a flexible opening is formed between the flexible member and body portion, the flexible opening being defined by an opening in the flexible member smaller than the distance between the divider end and the wrapped end, wherein the flexible opening is capable of guiding and positioning the foot to a predetermined arrangement with respect to the pad; and
a first tensioning band operatively coupled to first and second locations of an outer surface of the body portion, the first tensioning band operable to secure opposing first and second portions of the inner surface of the body portion in order to secure the outward protrusion of the pad against the foot in the predetermined position.

16. The garment of claim 15, wherein the pad is removably disposed between the guide sleeve and the body portion.

* * * * *